(12) United States Patent
Van Manen et al.

(10) Patent No.: US 11,992,701 B2
(45) Date of Patent: May 28, 2024

(54) MODULAR BRACHYTHERAPY APPLICATOR

(71) Applicant: NUCLETRON OPERATIONS B.V., Veenendaal (NL)

(72) Inventors: Jan Willem Van Manen, Veenendaal (NL); Eylem Arikan, Veenendaal (NL); Wilko Van Erp, Veenendaal (NL)

(73) Assignee: Nucletron Operations B.V., Veenendaal (NL)

( * ) Notice: Subject to any disclaimer, the term of this patent is extended or adjusted under 35 U.S.C. 154(b) by 0 days.

(21) Appl. No.: 17/593,760

(22) PCT Filed: Feb. 27, 2020

(86) PCT No.: PCT/NL2020/050128
§ 371 (c)(1),
(2) Date: Sep. 24, 2021

(87) PCT Pub. No.: WO2020/197379
PCT Pub. Date: Oct. 1, 2020

(65) Prior Publication Data
US 2022/0161056 A1 May 26, 2022

Related U.S. Application Data

(60) Provisional application No. 62/900,030, filed on Sep. 13, 2019, provisional application No. 62/824,484, filed on Mar. 27, 2019.

(51) Int. Cl.
*A61N 5/10* (2006.01)
(52) U.S. Cl.
CPC ......... *A61N 5/1002* (2013.01); *A61N 5/1007* (2013.01); *A61N 5/1016* (2013.01);
(Continued)

(58) Field of Classification Search
CPC .. A61N 5/1002; A61N 5/1007; A61N 5/1016; A61N 2005/1004; A61N 2005/1008
See application file for complete search history.

(56) References Cited

U.S. PATENT DOCUMENTS

2007/0276177 A1 11/2007 Van't Hooft
2008/0064916 A1* 3/2008 Mick .................... A61N 5/1016
600/6
(Continued)

FOREIGN PATENT DOCUMENTS

CN 107249689 A 7/2020
JP 2001046533 A 2/2001
(Continued)

OTHER PUBLICATIONS

International Search Report dated Apr. 9, 2020 in International Application No. PCT/NL2020/050128 (3 pages).
(Continued)

*Primary Examiner* — Samuel G Gilbert
(74) *Attorney, Agent, or Firm* — Bookoff McAndrews, PLLC

(57) ABSTRACT

Exemplary brachytherapy applicators may include an interstitial tube having a body with a proximal end and a distal end and a central conduit extending from the distal end of the body, wherein the central conduit includes a proximal opening, a distal opening, and a channel extending from the proximal opening to the distal opening, and wherein the proximal opening is offset from an axis of the body. The proximal opening may be configured to fluidly connect to a brachytherapy guide tube, and the channel of the central conduit may be dimensioned to receive at least one of a needle or a catheter therethrough.

21 Claims, 29 Drawing Sheets

(52) U.S. Cl.
CPC ............. *A61N 2005/1004* (2013.01); *A61N 2005/1008* (2013.01)

(56) References Cited

U.S. PATENT DOCUMENTS

| | | | |
|---|---|---|---|
| 2010/0069878 A1* | 3/2010 | Parsai | A61N 5/1016 604/500 |
| 2010/0286465 A1* | 11/2010 | Benson | A61M 25/0029 600/3 |
| 2011/0224478 A1 | 9/2011 | Hannoun-Levi et al. | |
| 2012/0029263 A1 | 2/2012 | Wardt et al. | |
| 2012/0277518 A1* | 11/2012 | Mick | A61N 5/1016 600/6 |
| 2013/0109908 A1 | 5/2013 | Rahimian | |
| 2013/0317276 A1* | 11/2013 | D'Andrea | A61N 5/1067 600/2 |
| 2014/0121444 A1 | 5/2014 | van Erp et al. | |
| 2015/0065784 A1* | 3/2015 | Fillmore | A61N 5/1014 600/8 |
| 2015/0327949 A1* | 11/2015 | Van De Wardt | A61B 90/39 600/417 |
| 2017/0291041 A1* | 10/2017 | Steller | A61N 5/1007 |

FOREIGN PATENT DOCUMENTS

| | | |
|---|---|---|
| NL | 1031785 C2 | 11/2007 |
| NL | 1035971 C | 3/2010 |
| NL | 2009697 C2 | 4/2014 |
| WO | 2010112172 A1 | 10/2010 |
| WO | 2016087946 A1 | 6/2016 |

OTHER PUBLICATIONS

Varian: "Varian Brachytherapy Applicators and Accessories", Jan. 1, 2011 (Jan. 1, 2011), XP055339041, Retrieved from the Internet: URL:https://www.varian.com/sites/default/files/resource attachments/Brachytherapy_Applicators Accessories_Catalogue_0_0.pdf (147 pages).

National Intellectual Property Administration, PRC, Application No. or patent No. 2020800397058, Notification of the First Office Action, 10 pages, Dec. 1, 2023, English Translation, China.

National Intellectual Property Administration, PRC, Application No. or patent No. 2020800397058, Notification of the First Office Action, 9 pages, Dec. 1, 2023, China.

Yuxia Lin et al., Posterior cervical cancer-loaded implant and radiotherapy 60-cases of nursing, Fujian Medical Journal, No. 05, Oct. 25, 2015, 2 pages. China.

* cited by examiner

MODULAR BRACHYTHERAPY APPLICATOR

CROSS-REFERENCE TO RELATED APPLICATIONS

This patent application is the U.S. national phase entry under 35 U.S.C. § 371 of International Application No. PCT/NL2020/050128, filed on Feb. 27, 2020, which claims the benefit of priority from U.S. Provisional Application No. 62/824,484, filed on Mar. 27, 2019, and U.S. Provisional Application No. 62/900,030, filed on Sep. 13, 2019, the entireties of each of which are incorporated herein by reference.

TECHNICAL FIELD

Various embodiments of the present disclosure relate generally to medical devices for brachytherapy. More specifically, embodiments of the present disclosure relate to brachytherapy applicators, and, in particular, to gynecological applicators.

INTRODUCTION

Brachytherapy may be used for the treatment of cancerous tissue, for example, tumors, and involves the placement of radioactive sources relative to the area of a subject (e.g., a patient) to be treated. Brachytherapy applicators may be used to promote accurate placement of radioactive sources, for example, interstitially or intracavitary. Variations in patient anatomy may render some conventional brachytherapy applicators cumbersome or unsuitable for accurately providing a pre-planned dose distribution inside the subject. Additionally, some conventional applicators may be generally rigid once assembled and may cause discomfort in patients. In particular, some gynecological brachytherapy applicators may cause introitus-related pain for subjects and/or may be too large for certain subjects. Conventional brachytherapy applicators may not fit—and thus may not function—ideally for women who have greater anatomical deviations, for example, those who do not have a uterus (e.g., following hysterectomy). In this group of patients, conventional brachytherapy applicators may provide less-effective treatment, or medical professionals may resort to manually placing needles free hand to deliver radioactive sources. Conventional modular brachytherapy applicators may further be more time-consuming to put together, with some parts requiring separate screws and/or tooling to attach different portions.

Brachytherapy applicators according to the present disclosure may solve one or more of the problems set forth above and/or other problems in the art. The current scope of the disclosure, however, is defined by the attached claims and not by the ability to solve any specific problem.

SUMMARY

Embodiments of the disclosure may be drawn to brachytherapy applicators. Exemplary applicators may include an interstitial tube having a body with a proximal end, a distal end, and a central conduit extending from the distal end of the body. The central conduit includes a proximal opening, a distal opening, and a channel extending from the proximal opening to the distal opening, and wherein the proximal opening is offset from an axis of the body. The proximal opening may be configured to fluidly connect to a brachytherapy guide tube, and the channel of the central conduit may be dimensioned to receive at least one of a needle or a catheter therethrough.

Various embodiments of the disclosure may include one or more of the following aspects: the applicator may further include a first connector attached to the body of the interstitial tube, and the first connector may have a first coupling surface that is configured to receive a second connector associated with an ovoid tube to couple the ovoid tube to the interstitial tube; the first connector may include a plurality of coupling surfaces; the applicator may further comprise a first ovoid tube and a second ovoid tube, wherein a second connector of the first ovoid tube may be configured to releasably couple with the first coupling surface, and wherein a second connector of the second ovoid tube may be configured to releasably couple with a second coupling surface of the plurality of coupling surfaces; the first ovoid tube may include a first ovoid located at a distal end of the first ovoid tube, and the second ovoid tube may include a second ovoid located at a distal end of the second ovoid tube, and the first ovoid and the second ovoid may cooperatively form a generally rectangular surface aligned around the central conduit when the second connector of the first ovoid tube and the second connector of the second ovoid tube are coupled with the first connector of the interstitial tube; the applicator may further comprise a rectal retractor configured to removably couple to the first connector, and at least one of a proximal end of the rectal retractor or a distal end of the rectal retractor may have a width that is greater than a central portion of the rectal retractor; or the applicator may further comprise at least one of a needle or a catheter having a distal portion dimensioned to extend into the proximal opening of the central conduit and through the central conduit so that a distal end of the needle or the catheter extends distally out of the distal opening of the central conduit when the needle or the catheter is positioned within the central conduit.

Embodiments of the disclosure may also be drawn to a brachytherapy applicator having an interstitial tube. The interstitial tube may include a body having a proximal end and a distal end, a joint located at a distal region of the body, wherein the joint has a proximal surface having an opening for coupling to a brachytherapy guide tube, and a central conduit extending distally from the joint, wherein the central conduit has a channel therethrough that fluidly connects with the opening in the joint and extends through a distal end of the central conduit so that the distal end of the central conduit is open. The applicator may also include a first ovoid tube having a first ovoid located at a distal end of the first ovoid tube and a second ovoid tube having a second ovoid located at a distal end of the second ovoid tube. The first ovoid and the second ovoid may cooperatively form a generally rectangular surface aligned around the central conduit when the first ovoid tube and the second ovoid tube are connected to the interstitial tube.

Various embodiments of the disclosure may include one or more of the following aspects: the applicator may further comprise a first connector attached to a central region of the body, wherein the first connector has at least two coupling surfaces and each coupling surface has an aperture therethrough, a second connector having an anchor extending therefrom associated with the first ovoid tube, and a second connector having an anchor extending therefrom associated with the second ovoid tube, wherein each aperture of the at least two coupling surfaces is dimensioned to receive one of the anchors of the second connectors within it to releasably couple the first ovoid tube or the second ovoid tube to the interstitial tube; the applicator may further comprise a rectal retractor configured to removably couple to the first connector, wherein at least one of a proximal end of the rectal retractor or a distal end of the rectal retractor has a width that is greater than a central portion of the rectal retractor; or the applicator may further comprise a spreading clip.

Embodiments of the disclosure may also be drawn to a kit for forming a modular brachytherapy applicator. The kit may include an interstitial tube having a body with a proximal end and a distal end and a central conduit extending from the distal end of the body, wherein the central conduit includes a proximal opening, a distal opening, and a channel extending from the proximal opening to the distal opening, and wherein a proximal end of the central conduit where the proximal opening is located is offset from an axis of the body. The kit may also include a first ovoid tube, a first ovoid, a second ovoid tube, and a second ovoid.

Various embodiments of the disclosure may include one or more of the following aspects: the first ovoid may be coupled to a distal end of the first ovoid tube, and the second ovoid may be coupled to a distal end of the second ovoid tube; the kit may further comprise a needle or a catheter having an outer diameter that is less than an inner diameter of the central conduit; the kit may further comprise a first connector coupled to the body of the interstitial tube, the first connector having a first coupling surface and a second coupling surface, wherein a second connector associated with the first ovoid tube is configured to releasably couple with the first coupling surface, and a second connector associated with the second ovoid tube is configured to releasably couple with the second coupling surface; the first ovoid and the second ovoid may cooperatively form a generally rectangular surface aligned around the central conduit when the second connector of the first ovoid tube is coupled to the first coupling surface and the second connector of the second ovoid tube is coupled to the second coupling surface; the kit may further comprise a rectal retractor configured to removably couple to the first connector, wherein at least one of a proximal end of the rectal retractor or a distal end of the rectal retractor may have a width that is greater than a central portion of the rectal retractor; the first ovoid and the second ovoid may be configured to releasably couple to the first ovoid tube or the second ovoid tube, respectively; the kit may further comprise a joint located at a distal region of the body, wherein the joint has a proximal surface that includes an opening configured to couple with a distal end of a brachytherapy guide tube, wherein the central conduit extends from a distal surface of the joint, and wherein the opening of the joint communicates with the channel of the central conduit; or the kit may further comprise the guide tube having the distal end configured to couple with the opening of the joint.

Additional objects and advantages of the disclosed embodiments will be set forth in part in the description that follows, and in part will be apparent from the description, or may be learned by practice of the disclosed embodiments.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and, together with the description, serve to explain the principles of the disclosed embodiments.

One skilled in the art would understand that, even if it is not specifically mentioned, aspects described with reference to one embodiment may also be applicable to, and may be used with, other embodiments. Moreover, there are many embodiments described and illustrated herein. The present disclosure is neither limited to any single aspect nor embodiment thereof, nor to any combinations and/or permutations of such aspects and/or embodiments. Moreover, each aspect of the present disclosure, and/or embodiments thereof, may be employed alone or in combination with one or more of the other aspects of the present disclosure and/or embodiments thereof. For the sake of brevity, certain permutations and combinations are not discussed and/or illustrated separately herein. Notably, an embodiment or implementation described herein as "exemplary" is not to be construed as preferred or advantageous, for example, over other embodiments or implementations; rather, it is intended to reflect or indicate that the embodiment(s) is/are "example" embodiment(s).

Figure 1A:
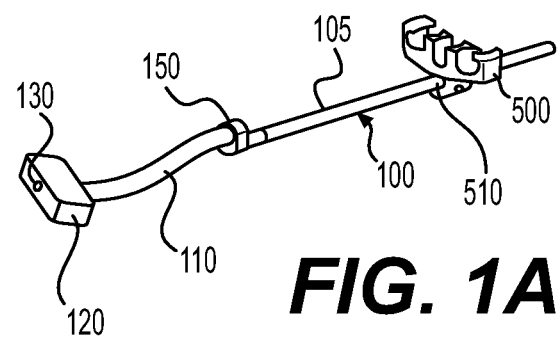
FIG. 1A illustrates an interstitial tube of a modular applicator and accompanying connector, according to one or more embodiments of the present disclosure.

Again, there are many embodiments described and illustrated herein. The present disclosure is neither limited to any single aspect nor embodiment thereof, nor to any combinations and/or permutations of such aspects and/or embodiments. Each of the aspects of the present disclosure, and/or embodiments thereof, may be employed alone or in combination with one or more of the other aspects of the present disclosure and/or embodiments thereof. For the sake of brevity, many of those combinations and permutations are not discussed separately herein.

DETAILED DESCRIPTION

It should be noted that the description set forth herein is merely illustrative in nature and is not intended to limit the embodiments of the subject matter, nor the application and uses of such embodiments. The terms "comprise," "include," "have," "with," and any variations thereof are used synonymously to denote or describe a non-exclusive inclusion. As such, a device or a method that uses such terms does not include only those elements or steps, but may include other elements and steps not expressly listed or inherent to such device and method. Further, the terms "first," "second," and the like, herein do not denote any order, quantity, or importance, but rather are used to distinguish one element from another. Similarly, terms of relative orientation, such as "top," "bottom," etc. are used with reference to the orientation of the structure illustrated in the figures being described. The term "distal" refers to the direction that is away from the user or operator and into the subject. By contrast, the term "proximal" refers to the direction that is closer to the user or operator and away from the subject. Moreover, the terms "a" and "an" herein do not denote a limitation of quantity, but rather denote the presence of at least one of the referenced item. It should be noted that all numeric values disclosed or claimed herein (including all disclosed values, limits, and ranges) may have a variation of +/−10% (unless a different variation is specified) from the disclosed numeric value. In this disclosure, unless stated otherwise, relative terms, such as, for example, "about," "substantially," and "approximately" are used to indicate a possible variation of +/−10% in the stated value. Moreover, in the claims, values, limits, and/or ranges of various claimed elements and/or features means the stated value, limit, and/or range +/−10%.

Embodiments of the disclosure are drawn to modular applicators, and, in particular, to gynecological brachytherapy applicators, although the disclosure is not necessarily limited to applicators for gynecological uses. Exemplary applicators may be configured to make more areas of the body accessible for delivering radiation. For example, applicators of the present disclosure may permit a healthcare provider to use the applicator to deliver radioactive material to the body along a central region of an applicator, as opposed to traditional gynecological applicators, which may only allow for dosage delivery along a lateral region of the applicator. In some embodiments, the exemplary applicators may be utilized to access tumorous tissues around a vaginal cuff of a patient by positioning the central region of the applicator below a surface of a cervical stopper (i.e., collar) of the applicator. Providing a central region to administer a radioactive source from may allow for more optimal coverage of a target treatment volume while reducing or eliminating radioactive "hot" or "cold" spots therein, and/or administration of an excessive dose to various organs at risk. Whereas traditional gynecological applicators may include hollow shafts on either side of the applicators to allow for the passage of radioactive material to lateral positions within the patient, exemplary applicators of the disclosure may include a central conduit configured to permit delivery of radioactive material to a region of the body adjacent the central portion of the applicator. Exemplary applicators may include an interstitial tube having an open end to allow for the passage of a needle or a catheter therethrough. Once placed, during treatment, radioactive material (e.g., a radioactive source) may be delivered through the interstitial tube via a needle or catheter to this central region of the patient.

High dose rate brachytherapy involves utilizing high energetic isotopes in radiation therapy to treat a target treatment site within a patient. A treatment plan may include determining a relative position of the applicator within a patient to ensure a target treatment site and/or volume is accessible for receipt of a radioactive source to be delivered by the applicator. The applicator may be positioned so that the target volume is encompassed by the applicator prior to delivery of the radioactive source. A position of the radioactive source within the applicator may be determined based on various parameters, including, but not limited to, one or more of a geometry of the applicator, a patient's anatomy, or a shape of the target treatment site.

A radiation treatment planning application may be formulated to determine the respective radiation source positions based on at least the parameters described above. A remote after-loader containing the radioactive source may be operably coupled to the applicator for transferring the radioactive source from the after-loader and into the applicator in accordance with the treatment plan. Particularly, the remote after-loader may be used to move the radioactive source to one or more channels of the applicator for delivery to a patient's target treatment site(s). A treatment plan executed by the after-loader may further define predetermined delivery positions, dwell times, and dose volumes for radiating a patient's target treatment site.

In some embodiments, the size, shape, or arrangement of the applicators described herein may be configured to facilitate the delivery of radiation to a patient, to increase accuracy of treatment plan execution, or to increase patient comfort. In some embodiments, modular applicators may further be designed to be easily assembled and disassembled by a user to promote ease of use or to allow for customization of the applicator to an individual patient. Specific examples of applicators are now described herein.

Figure 1B:
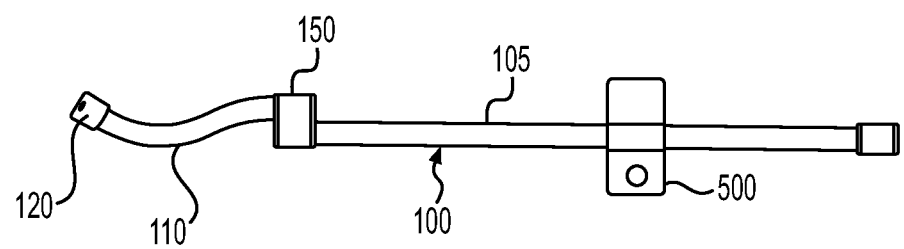
FIG. 1B is a side view of the interstitial tube shown in FIG. 1A.
Figure 1C:
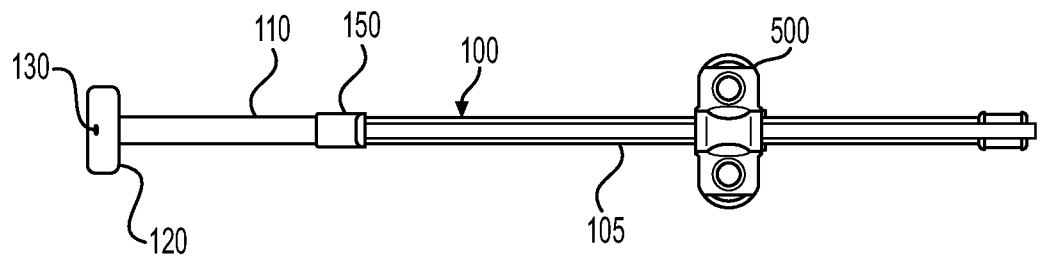
FIG. 1C is a top view of the interstitial tube shown in FIGS. 1A and 1B.

FIGS. 1A-1C illustrate different views of components of a modular applicator, including an interstitial tube 100 and a first connector 500. The interstitial tube 100 may be configured to couple with one or more peripheral elements, for example, one or more ovoid tubes 200, 200' (FIG. 2A), one or more guide tubes 600 (FIG. 2C), and/or rectal retractor 400 (FIG. 3A), as will be described further below. This coupling may be facilitated by first connector 500 or other suitable components (e.g., first connectors 500', 550, 550'), as will be described in greater detail herein.

Interstitial tube 100 may include a main body 105 having a proximal end and a distal end. Main body 105 may have a generally tubular shape, although any cross-sectional shape may be suitable (e.g., oval, rectangular, etc.). Interstitial tube 100 may include a distal central conduit 110, a collar 120, a distal opening 130, and/or a joint 150. The central conduit 110 may extend distally from the distal end of main body 105 via the joint 150. In some embodiments, the axis of main body 105 may be offset from the axis of central conduit 110, and main body 105 may couple to joint 150 at a location that is axially offset from central conduit 110, as is shown in FIGS. 1A-1C, 1E, 1F, and 4. This axially offset positioning may allow a guide tube 600 (FIGS. 1E and 1F) to couple to joint 150 of interstitial tube 100 so that guide tube 600 is aligned with central conduit 110, 110'. This may in turn allow a needle or catheter 300 to be inserted through guide tube 600 and through central conduit 110, 110' of interstitial tube 100, as will be described in further detail below. Interstitial tube 100 may be particularly useful when assembling and customizing a modular applicator for use with a patient who has undergone hysterectomy or otherwise may require radiation in a portion of the anatomy that will be in line with a distal, central region of the applicator, once inserted into the subject.

Figure 1D:
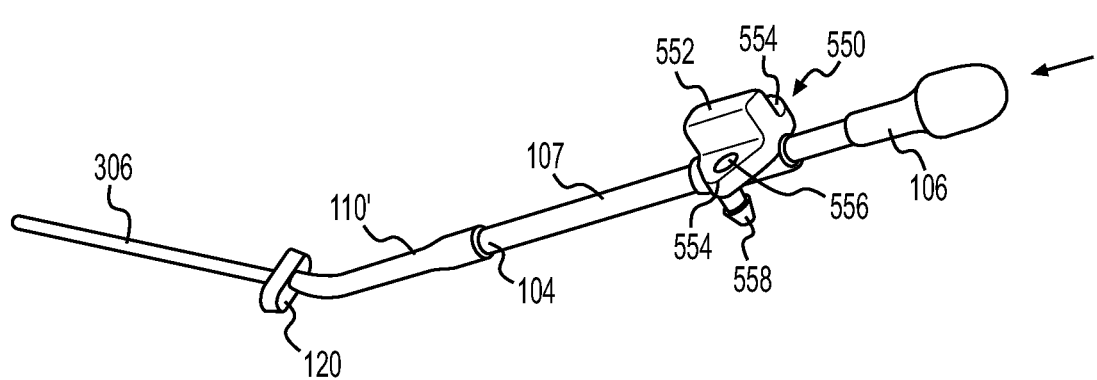
FIG. 1D is a perspective view of an intrauterine (IU) tube with an exemplary first connector, according to one or more embodiments of the present disclosure.

In other embodiments, modular applicators of the present disclosure may be used with an intrauterine (IU) tube 107 (as opposed to an interstitial tube 100). If an IU tube 107 is used in place of an intrauterine IU tube 100, distal central conduit 110 may extend distally from the distal end of main body 105 of IU tube 107 without the joint 150 disposed therebetween, such that distal central conduit 110 extends from the distal end of IU tube 107 (FIG. 1D). If an IU tube 107 is used, the axis of main body 105 may align with the axis of distal central conduit 110, and main body 105 may not be configured to receive a needle or catheter 300 therethrough. Further, IU tube 107 may include a distal projection 306 extending from collar 120 configured to facilitate positioning the applicator relative to the cervix. Modular applicators of the present disclosure are depicted with either IU tube 107 or interstitial tube 100 interchangeably, because both may be used interchangeably depending on which is indicated based on the anatomy and/or treatment protocol of an individual patient. Accordingly, components of modular applicators described herein may be used with either IU tube 107 or interstitial tube 100.

Figure 1E:
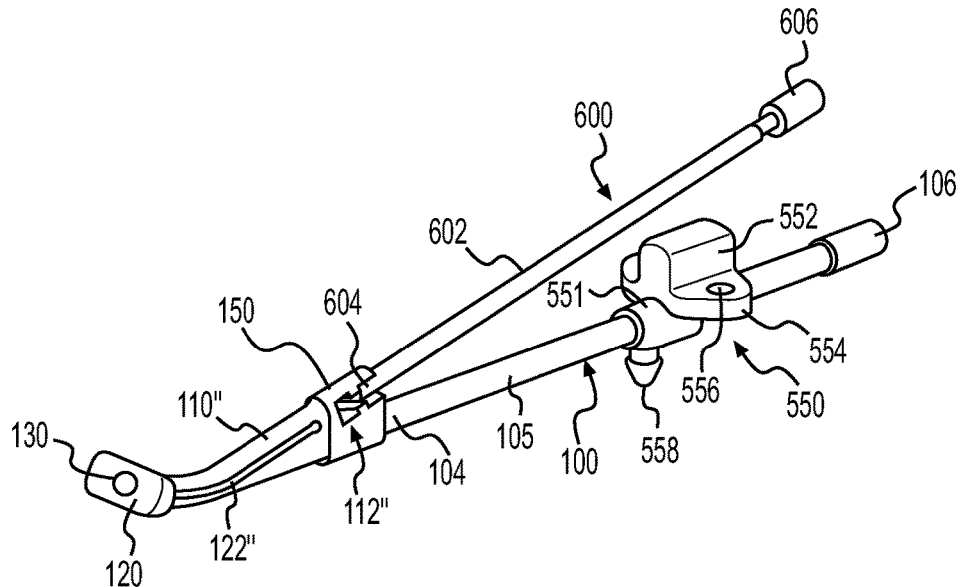
FIG. 1E is a perspective view of an interstitial tube with guide tube secured thereto, according to one or more embodiments of the present disclosure.
Figure 1F:
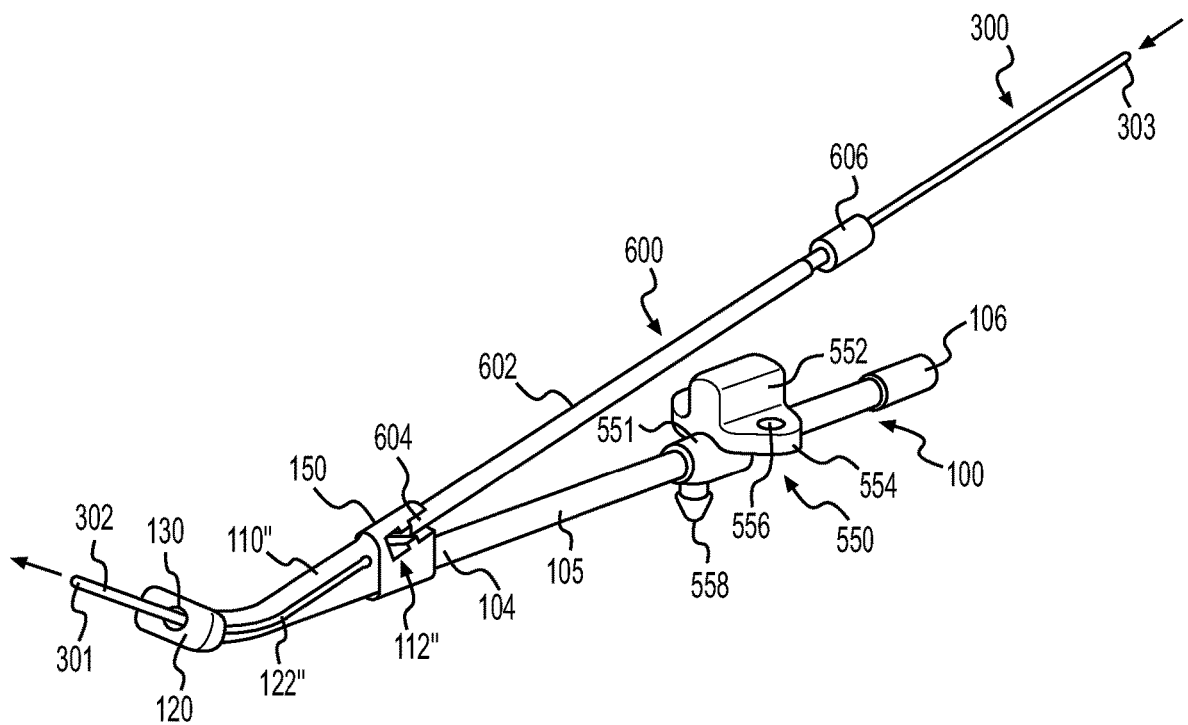
FIG. 1F is a perspective view of the interstitial tube shown in FIG. 1E with a needle inserted through the guide tube.

Turning back to the interstitial tubes 100 of FIGS. 1A-1C, 1E, and 1F, guide tube 600, which may be sold together with other components of the applicator or may be sold separate from other components of the applicator, may have a distal end configured to couple to joint 150. For example, joint 150 may include a recessed female portion into which a distal end of guide tube 600 may be received, or vice versa. The recessed portion of joint 150 may have a shape that complements the shape of the distal region of guide tube 600. Guide tube 600 may connect to the recessed portion of joint 150 by a snap-fit, friction-fit, screw-fit, bayonet-fit, or any other suitable type of connection. In some embodiments, a central or proximal region of guide tube 600 may rest on first connector 500 or may be coupled to the first connector 500. For example, guide tube 600 may pass through or be received by a lumen, bore, hole, slot, recess, notch, anchor, clasp, or other suitable securing mechanism of first connector 500. In other aspects, as shown in FIGS. 1E and 1F, guide tube 600 may extend separate from a first connector when connected to joint 150.

A portion of joint 150 that connects with the distal end of guide tube 600 may fluidly connect with a channel extending through central conduit 110, 110'. Accordingly, a channel extending through guide tube 600 may fluidly connect with the channel extending through central conduit 110, 110' when guide tube 600 is connected to joint 150. When guide tube 600 is connected to joint 150, the openings in guide tube 600, joint 150, central conduit 110, 110', and collar 120 may align, creating a channel that extends from the proximal end of guide tube 600 through collar 120 to distal opening 130. The inner channel along guide tube 600 may be dimensioned to receive a needle or catheter within it. This may allow needle 300 (FIGS. 1F and 4) to be inserted through guide tube 600, through joint 150, through central conduit 110, 110', and out the distal opening 130, to extend distally past the distal surface of the collar 120.

Accordingly, central conduit 110 of interstitial tube 100 may have an inner diameter that is sufficient to allow a needle 300 to pass through the central conduit 110. For example, central conduit 110 may have an inner diameter of 1 millimeter (mm) to 10 mm, less than or equal to 10 mm, less than or equal to 8 mm, less than or equal to 6 mm, 6 mm to 10 mm, less than or equal to 5 mm, 1 mm to 6 mm, less than or equal to 4 mm, less than or equal to 3 mm, less than or equal to 2.5 mm, less than or equal to 2 mm, less than or equal to 1.5 mm, 1.5 mm to 5 mm, 1.5 mm to 3 mm, or 1.5 mm to 2.5 mm (e.g., 2.1 mm). The central conduit 110 may be a continuous channel extending from the joint 150 to collar 120. In some embodiments, collar 120 may have a height and/or a width that is greater than an outer diameter of the central conduit 110. For example, collar 120 of distal central conduit 110 may include a width and/or diameter that is about 4 millimeters, however, this is only exemplary.

Figure 2A:
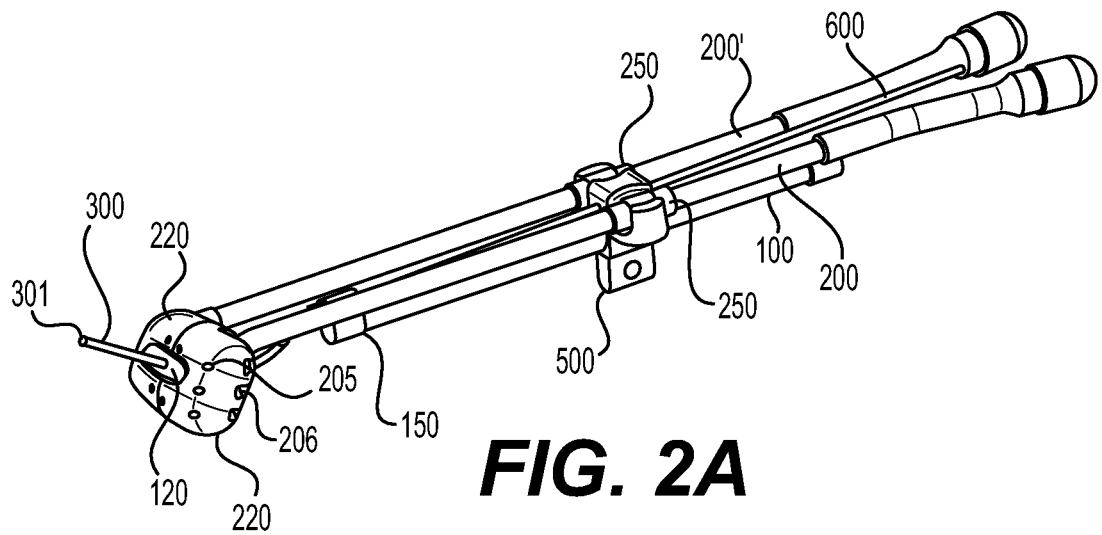
FIG. 2A is a perspective view of a modular applicator, according to one or more embodiments of the present disclosure.
Figure 2B:
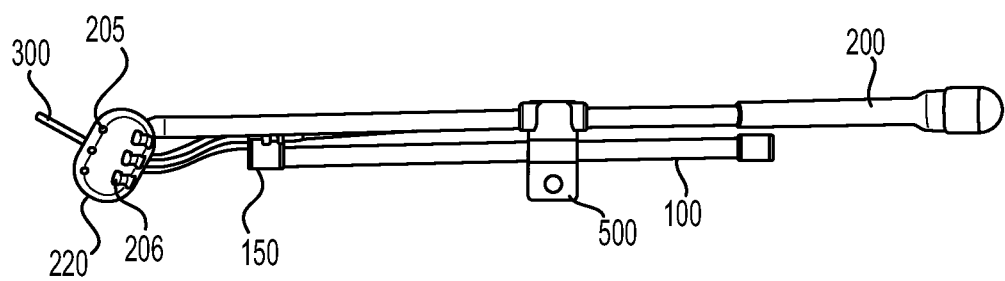
FIG. 2B is a side view of the modular applicator shown in FIG. 2A.
Figure 2C:
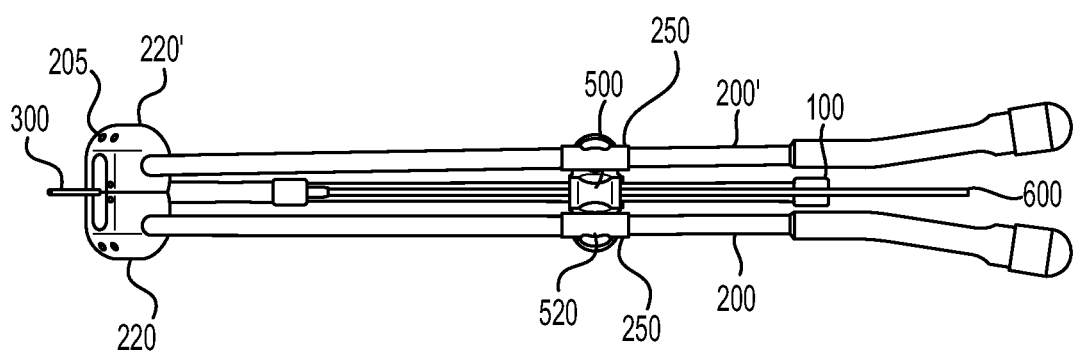
FIG. 2C is a top-down view of the modular applicator shown in FIGS. 2A and 2B.

Collar 120 may be configured to align with one or more ovoids 220, 220' associated with ovoid tubes 200, 200', as is shown in FIGS. 2A-2C and described in more detail below. When ovoid tubes 200, 200' are connected to interstitial tube 100 (or IU tube 107, depending on which is selected for use with a given patient), ovoids 220, 220' may be positioned around collar 120 and, in some embodiments, may attach to collar 120. Accordingly, when ovoids 220, 220' are positioned around collar 120, central conduit 110 may extend through a central region of the ovoids 220, 220'. The collar 120 may have a distal opening 130 configured to allow a distal portion of needle 300 to extend from the central conduit 110 past the distal surface of the collar 120 when needle 300 is inserted through interstitial tube 100 (or IU tube 107).

Interstitial tube 100 (or IU tube 107) may be generally tubular, although interstitial tube 100 may have any suitable cross-sectional shape (e.g., oval, rectangular, etc.) extending from a proximal end to a distal end. In some embodiments, interstitial tube 100 may be hollow and may have a sufficient diameter to allow a needle 300 or catheter, e.g., a needle or catheter containing a radioactive source, to pass through interstitial tube 100. Needle 300 may also optionally include an opening at a distal end 301. Collar 120 of interstitial tube 100 (or IU tube 107) may include distal opening 130, which may allow a needle (e.g., a ProGuide needle sold by Nucletron) or catheter to pass through the length of central conduit 110 of interstitial tube 100 and for a distal portion of the needle 300 or catheter to be extended distally out of the distal opening 130 of interstitial tube 100 to a location distally beyond interstitial tube 100. Accordingly, needle 300 containing a radioactive source may be inserted into guide tube 600, and a distal portion of needle 300 may be positioned to extend into central conduit 110 and, if desired for treatment, beyond distal opening 130 of collar 120. In this manner, it may be possible to position a radioactive source in a central region of the body in which the applicator is located and/or to a position that is distal to the distal end of the applicator.

By including interstitial tube 100 with a hollow central conduit 110, 100' and a distal opening 130, applicators of the present disclosure may be able to deliver a conformal dose of radiation not only laterally, via ovoid tubes 200, 200' and/or needles or catheters positioned therethrough or around the applicator, but also in a central region of the subject. This may be of particular importance for women who have undergone a hysterectomy and who have tumorous tissue growing around the cervix, or the region where the cervix once was. Traditional applicators may only allow radioactive material to be delivered laterally along the applicators by way of ovoid tubes or peripheral needles, making it impossible to deliver radioactive material to this central, distal region of the applicator. Being limited to only lateral dose delivery may lead to over-treatment and/or under-treatment of healthy and/or cancerous tissue, because tumor tissue in the middle region of the patient anatomy couldn't be easily accessed for administering radiation. Indeed, as alluded to previously, some clinicians opted to insert needles freehand in order to access the central region of the patient anatomy. As a result, subjects requiring treatment to target areas adjacent this central region have been difficult to treat. By contrast, the incorporation of interstitial tube 100 with an open distal end may allow a physician to more precisely deliver radioactive material to this central region of the body. As a result, the novel applicators described herein may increase source positioning accuracy and dose accuracy.

In one or more embodiments, central conduit 110 may be configured to receive needles 300 of different dimensions and/or sizes. Exemplary needles 300 may have a diameter of 1 mm to 10 mm, less than or equal to 10 mm, less than or equal to 8 mm, less than or equal to 6 mm, 6 mm to 10 mm, less than or equal to 5 mm, 1 mm to 6 mm, less than or equal to 4 mm, less than or equal to 3 mm, less than or equal to 2.5 mm, less than or equal to 2 mm, less than or equal to 1.5 mm, 1.5 mm to 5 mm, 1.5 mm to 3 mm, or 1.5 mm to 2.5 mm. Accordingly, central conduit 110 may have an inner channel with an inner diameter that is greater than an outer diameter of a needle 300 to be received within the channel. Central conduit 110 of interstitial tube 100 may have outer diameters ranging, e.g., from approximately 2 mm to approximately 8 mm, for example, 2 mm or 4 mm, e.g., 3.85 mm. The inner diameters of central conduits 110 may be sized to accommodate standard needles and/or catheters, for example, to accommodate a 2 mm needle or a ¾ mm catheter.

Interstitial tube 100 (or IU tube 107) may have a standard shape and size for all patients or may come in different lengths, widths, and/or different configurations of central conduit 110 to accommodate different treatment regions and/or differences in patient anatomy. For example, in some embodiments, the central conduit 110 of interstitial tube 100 may be straight or curved, may be angled, may be flexible or more rigid, or may have different lengths. The shape and size of central conduit 110 may be formed to accommodate a variety of different needles 300 or catheters having different shapes and/or sizes or may be sized and shaped to accommodate a specific size and/or shape of needle 300 or catheters. As a result, applicators described herein may be able to accommodate a range of different needles 300 and a range of patient anatomies including, for example, anatomies of various sizes, anatomies with different target tissue regions to be treated, anatomies having different stages of disease, and/or anatomies with and without a uterus, depending on the type of interstitial tube 100 or IU tube 107 used. In other embodiments, interstitial tube 100 and central conduit 110 may be shaped and sized to consistently place needles 300 with an outer diameter of 2 mm at a predetermined insertion depth within a subject. In some embodiments, needles 300 may be configured to snap-fit, friction-fit, and/or click in place relative to central conduit 110. For example, needle 300 may include one or more stoppers configured to engage with one or more of central conduit 110, joint 150, and/or guide tube 600 to position needle 300 in place within the applicator, or vice versa.

Referring now to FIG. 1D, in some embodiments, a modular applicator may include an exemplary first connector 550 coupled to IU tube 107 (or an interstitial tube 100), along an intermediate portion of IU tube 107 between a distal end 104 and a proximal end 106. First connector 550 may function similarly to first connector 500 in that it may secure ovoid tubes 200, 200' in place and may secure rectal retractor 400 in place to form a modular applicator. First connector 550 may be used with an IU tube 107 or an interstitial tube 100, as described below.

First connector 550 includes a body 551 that is configured to receive a main body of IU tube 107 (shown in FIG. 1D) or of interstitial tube 100 therein to couple first connector 550 to IU tube 107 or interstitial tube 100. First connector 550 may allow one or more peripheral elements to connect to IU tube 107 or interstitial tube 100 (e.g., one or more ovoid tubes 200, 200' (FIGS. 2A-2D) or rectal retractor 400 (FIGS. 3A-3F)), as will be described further herein. First connector 550 includes a central divider 552 and a pair of lateral flanges 554 extending outward from central divider 552.

Figure 8A:
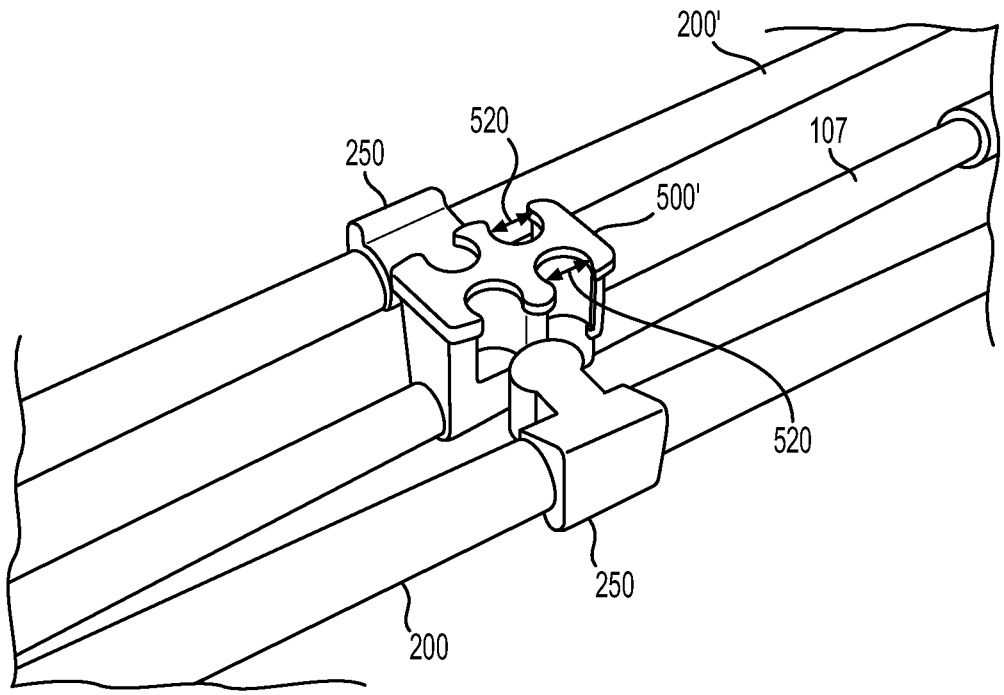
FIG. 8A illustrates portions of an IU tube, a first connector, a second connector, and an ovoid tube in an uncoupled state, according to one or more embodiments of the present disclosure.
Figure 8B:
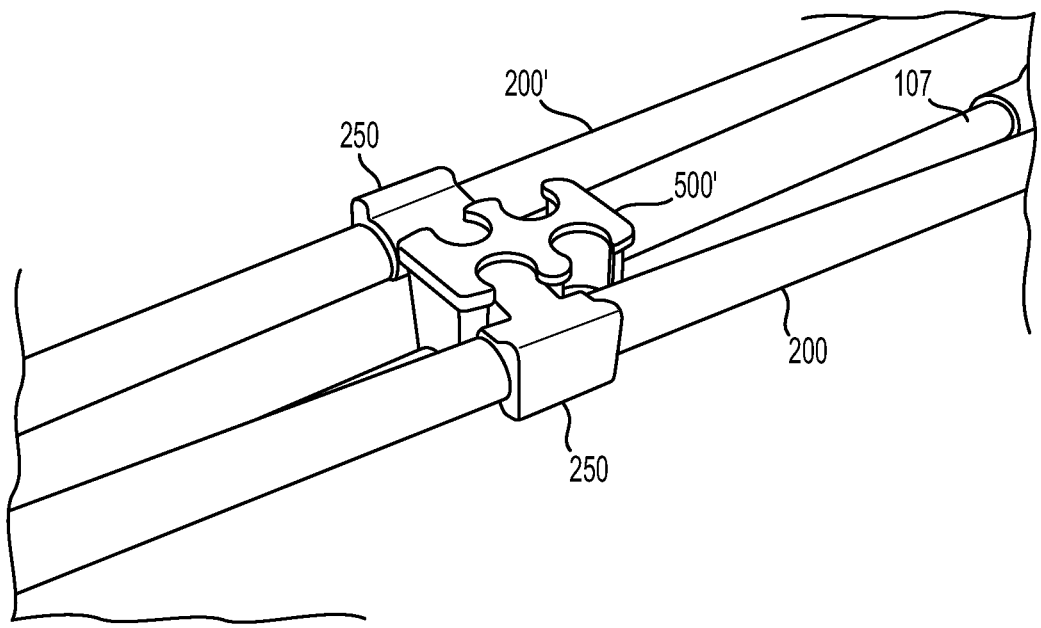
FIG. 8B illustrates the IU tube, the first connector, the second connector, and the ovoid tube shown in FIG. 8A, in a coupled state.
Figure 8C:
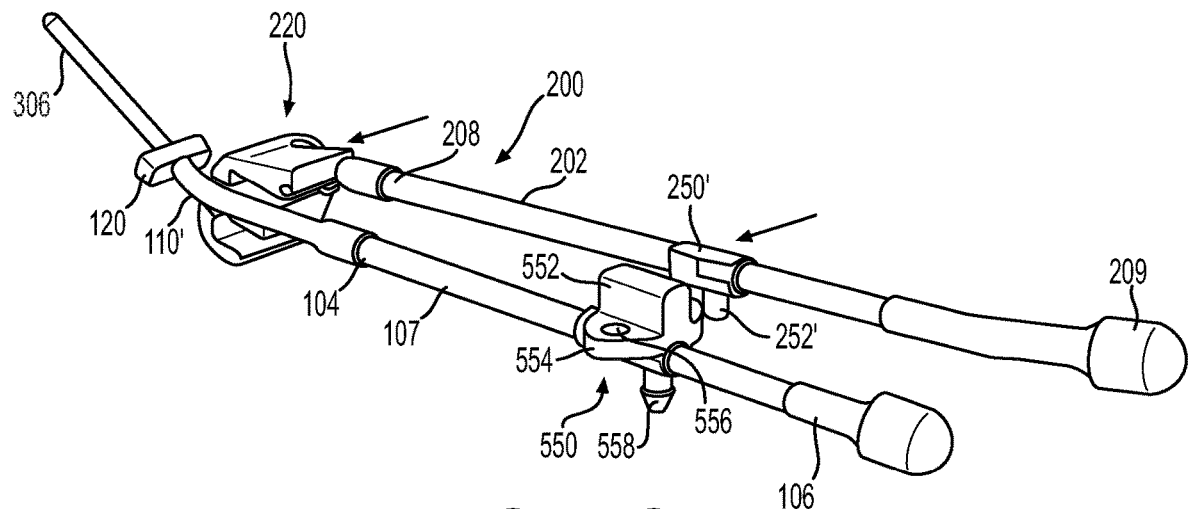
FIG. 8C is a perspective view of an IU tube, a first connector, a second connector, and an ovoid tube in an uncoupled state, according to one or more embodiments of the present disclosure.
Figure 8D:
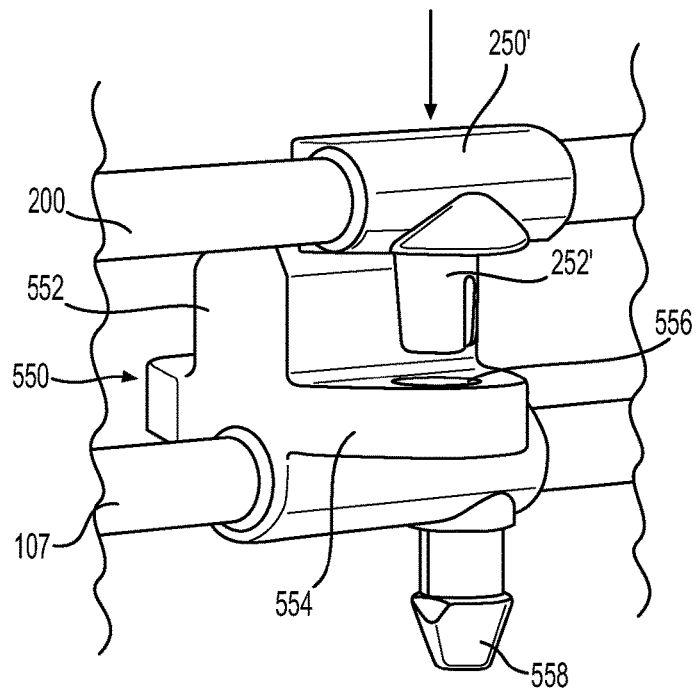
FIG. 8D is a partial perspective view of the IU tube, the first connector, the second connector, and the ovoid tube shown in FIG. 8C in an uncoupled state.

Each lateral flange 554 defines a coupling surface configured to receive one or more peripheral elements thereon (e.g., ovoid tubes 200, 200'). For first connector 550, the coupling surface of each lateral flange 554 includes an aperture 556 extending at least partially therethrough that is configured to couple with a projection of a second connector associated with the one or more peripheral elements received along the planar coupling surfaces to first connector 550. For example, an anchor 252' of a second connector 250' may be configured to mate (e.g., snap fit or friction fit) with an aperture 556 to secure an ovoid tube 200, 200' to first connector 550 (FIGS. 8C-8D). It should be appreciated that first connector 550 may be configured to at least partially inhibit release of anchor 252' of second connector 250' from within aperture 556, such as, for example, up to a predetermined extraction force.

First connector 550 further includes a protrusion 558 extending outwardly from body 551 in a direction opposite of central divider 552. Protrusion 558 is configured to secure first connector 550 to one or more peripheral elements of a modular applicator, for example, rectal retractor 400 (FIGS. 3D-3F).

Figure 3A:
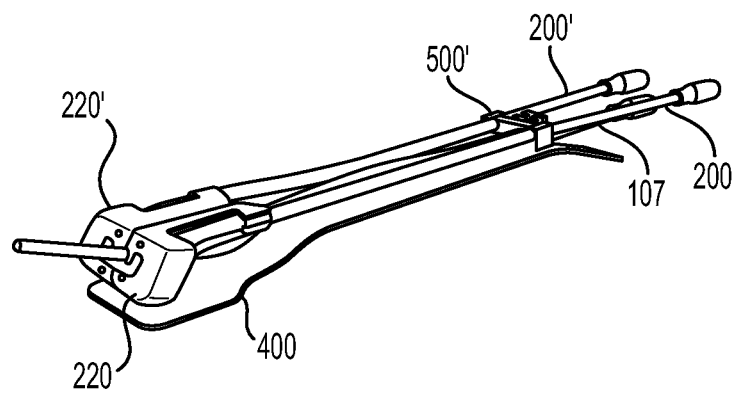
FIG. 3A is a perspective view of a modular applicator, according to one or more embodiments of the present disclosure.
Figure 3B:
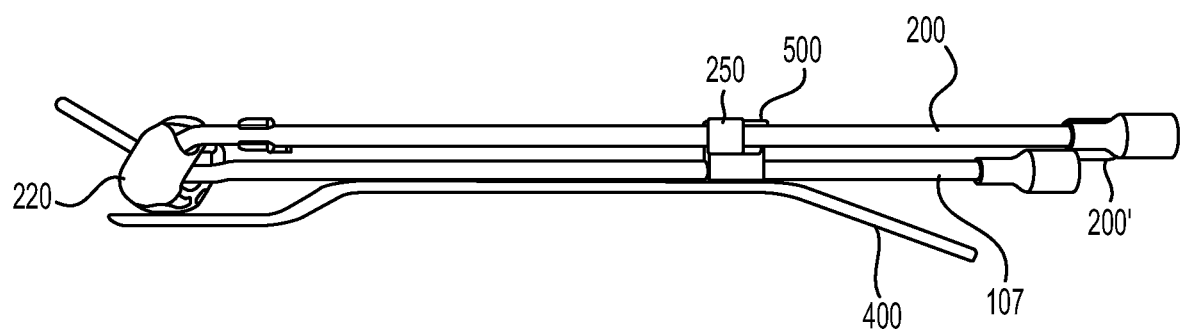
FIG. 3B is a side view of the modular applicator shown in FIG. 3A.
Figure 3C:
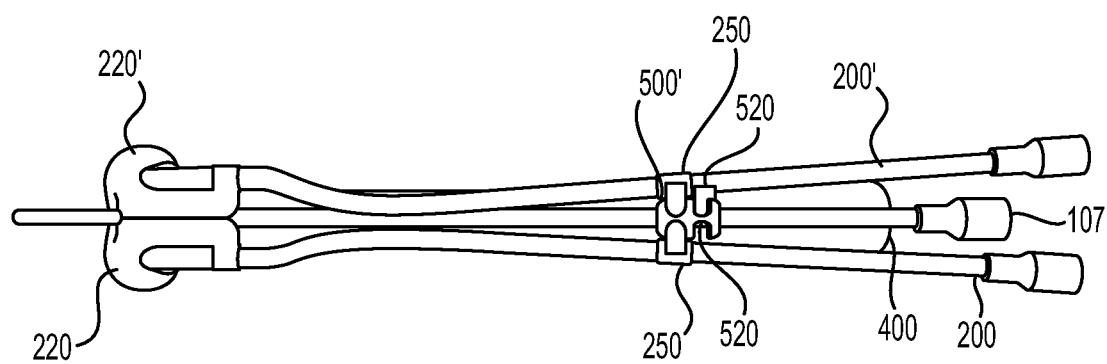
FIG. 3C is a top-down view of the modular applicator shown in FIGS. 3A and 3B.

Referring to FIGS. 3A-3C, in some embodiments, a modular applicator may further include rectal retractor 400. The rectal retractor 400 may be coupled to the interstitial tube 100 (or IU tube 107) via, for example, first connector 500, 500', 550, 550'. In exemplary embodiments, rectal retractor 400 may be attached to the applicator without the need for additional parts and/or tooling. Rectal retractor 400 may be configured to shield, e.g., create a distance between a radioactive source and the rectum. In some embodiments, rectal retractor 400 may be sized and shaped to reduce introitus-related discomfort associated with some conventional applicators.

Figure 3D:
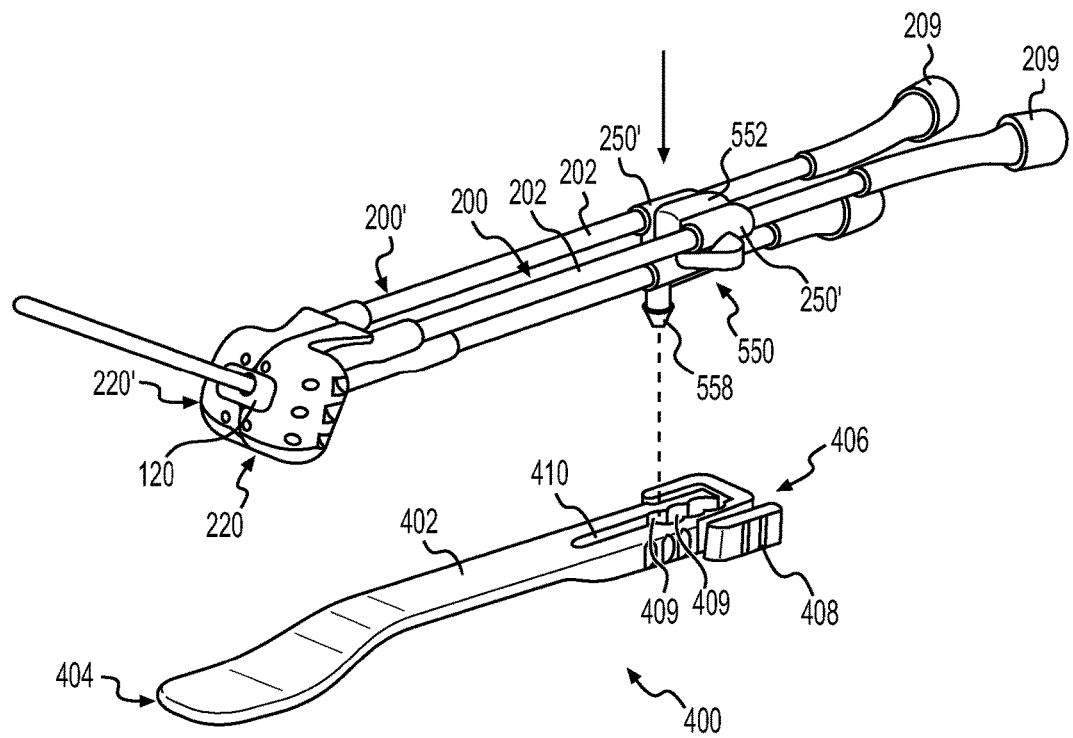
FIG. 3D is a perspective view of the modular applicator and an exemplary rectal retractor prior to attachment to the modular applicator, according to one or more embodiments of the present disclosure.
Figure 3E:
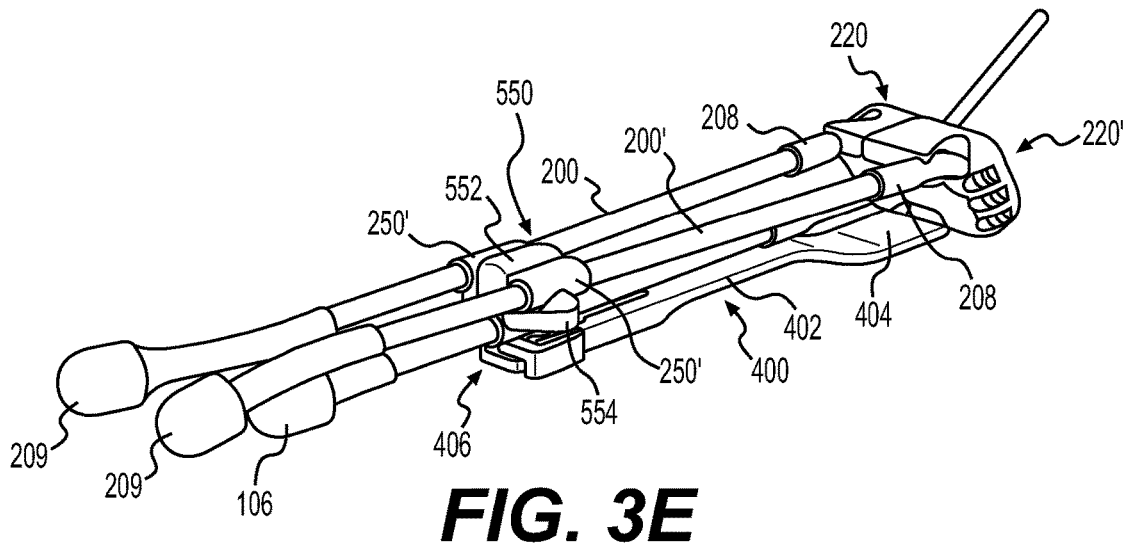
FIG. 3E is a perspective view of the modular applicator coupled to the rectal retractor shown in FIG. 3D.
Figure 3F:
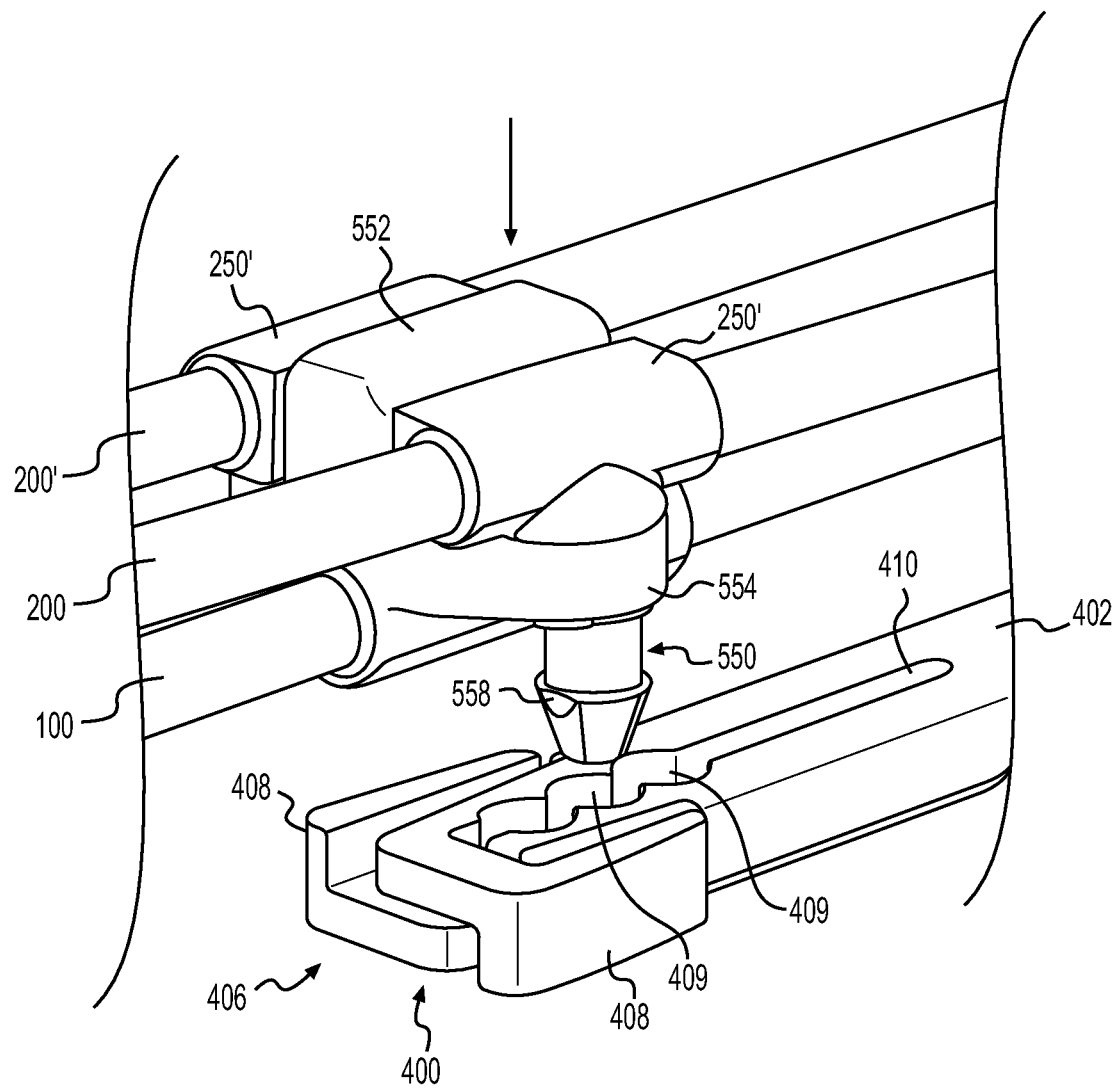
FIG. 3F is a partial perspective view of the modular applicator coupling to the rectal retractor shown in FIG. 3D.

As shown in FIG. 3D, for example, rectal retractor 400 may include a body 402 extending between a distal end 404 and a proximal end 406. The distal end 404 of rectal retractor 400 may include rounded edges and/or a tapered distal edge to reduce a distance between rectal retractor 400 and ovoid tubes 200, 200' at the introitus when rectal retractor 400 is coupled to the modular applicator and positioned within a subject. It should be appreciated that rectal retractor 400 may be configured to reduce a stress imparted on a subject's skin by including rounded/curved edges. In other embodiments, rectal retractor 400 may have one or more curves or contours along body 402 to promote patient comfort.

As seen in FIGS. 3A-3E, rectal retractor 400 may include at least two bends forming at least one point along the length of rectal retractor 400 in which the overall height of the modular applicator, when assembled, is less than the height of the modular applicator at the proximal end of rectal retractor 400, and less than the height of modular the applicator at the distal end of rectal retractor 400. In some embodiments, at a point along the length of rectal retractor 400 where the overall height of the modular applicator is less than the height of the modular applicator at the proximal end or the distal end of rectal retractor 400, the width of rectal retractor 400 may also be less than the width of rectal retractor 400 at the proximal end or the distal end of rectal retractor 400.

Alternatively, rectal retractor 400 may include a single bend between distal end 404 and proximal end 406 such that a height of rectal retractor 400 at either proximal end 406 or distal end 404 is relatively less. It should be understood that body 402 of rectal retractor 400 may include other suitable bends, curves, heights, widths, and/or configurations than those shown and described herein configured to reduce introitus-related discomfort associated with conventional applicators.

Further, to increase patient comfort, in some aspects, the width of rectal retractor 400 may be less than a width of the modular applicator when assembled or less than a width of ovoids 220, 220'. Exemplary dimensions of rectal retractor 400 may include, for example, a length from distal end 404 to proximal end 406 of about 10 millimeters to about 20 millimeters, and a width of about 6.5 millimeters to about 7.5 millimeters. In other embodiments, body 402 may have a length of about 30 to about 40 millimeters and a width of about 10 millimeters. It should be understood, however, that these dimensions are only exemplary.

Additionally or alternatively, as shown in FIGS. 3A-3C, in some aspects, the ovoid tubes 200, 200' of the modular applicator may be curved such that, when assembled, there exists a point along the length of the modular applicator at which the width of the modular applicator is less than the width of the modular applicator at the proximal end or the distal end, or both. Accordingly, rectal retractor 400 and/or the modular applicator overall may narrow in a central region. As a result, the overall shape and size of the modular applicator may reduce introitus-related discomfort associated with some conventional applicators.

Like ovoid tubes 200, 200', rectal retractor 400 may be configured to couple and uncouple from the modular applicator, for example, via first connector 550, 550'. Referring to FIGS. 3D and 3E, in some embodiments, rectal retractor 400 may include one or more engagement slots 410 extending along body 402 (e.g., in a proximal region). The engagement slot may include one or more (e.g., two, three, or four) widened apertures 409 sized and shaped to receive one or more coupling features therein for attaching rectal retractor 400 to the modular applicator, such as, for example, protrusion 558 of first connector 550. Rectal retractor 400 may receive protrusion 558 of first connector 550 within an aperture 409 to connect rectal retractor 400 to the modular applicator. In this way, rectal retractor may snap fit or friction fit to first connector 550. Additionally, by having multiple apertures 409, rectal retractor 400 may be affixed to the modular applicator in different positions.

In some aspects, longitudinal engagement slot 410 and apertures 409 may be configured to receive protrusion 558 of connector 550 and permit linear translation of protrusion 558 between multiple apertures 409. In other aspects, once protrusion 558 is received within an aperture 409, linear translation of protrusion 558 may be inhibited, and protrusion 558 may be fixed in place in the selected aperture 409. Apertures 409 may be offset relative to one another at various increments, such as, for example, increments of about 1 mm, about 2 mm, about 3 mm, about 4 mm, about 5 mm, about 6 mm, or about 7 mm. Accordingly, a relative position of interstitial tube 100, ovoid tubes 200, 200', and/or ovoids 220, 220' of the modular applicator relative to body 402 of rectal retractor 400 may be selectively adjustable.

Proximal end 406 of rectal retractor 400 may also include one or more flex tabs 408. Flex tabs 408 may be configured to release protrusion 558 from the one or more apertures 409. As shown in FIG. 3F, each flex tab 408 may be connected to an opposite side of slot 410. When flex tabs 408 are squeezed (e.g., flex tabs 408 are moved closer to one another), it may in turn push the opposite sides of slot 410, along which apertures 409 are positioned, away from each other. This may widen slot 410 and apertures 409, thereby releasing protrusion 558 from an aperture 409. In some aspects, tabs 408 may also be squeezed by a user when affixing rectal retractor 400 to first connector 550 to facilitate insertion of protrusion 558 into aperture 409.

Turning back to collar 120, collar 120 of distal central conduit 110' may be angled relative to a proximal region of distal central conduit 110'. For example, collar 120 may be angled relative to a proximal region of distal central conduit 110' by anywhere from about 5 to about 45 degrees, e.g., about 5 degrees, about 10 degrees, about 15 degrees, about 20 degrees, about 30 degrees, about 40 degrees, about 45 degrees, or other suitable angle. Further, distal central conduit 110' may extend different lengths between collar 120 and a proximal region, such as, for example, lengths ranging from about 30 mm to about 80 mm.

As described in greater detail herein, collar 120 may include one or more engagement features disposed thereon (e.g., one or more chamfers, protrusions, ridges, and/or recesses) for securely grasping, guiding, and/or aligning one or more ovoids 220 relative to collar 120. For example, the one or more engagement features may be disposed along a proximal portion of collar 120 to minimize a lateral profile of collar 120, although one or more engagement features may be included along the edges of collar 120.

Referring now to FIG. 1F, a guide tube 600 is shown connecting to a version of interstitial tube 100 having an angled distal central conduit 110". Distal central conduit 110" may otherwise be substantially similar to distal central conduit 110 of interstitial tube 100, described above. For example, distal central conduit 110" may include a collar 120 and a distal opening 130 disposed along a distal surface of collar 120. Distal central conduit 110" includes an inner channel 122" extending from a proximal end of distal central conduit 110" to distal opening 130 at collar 120. Inner channel 122" may be sized, shaped, and configured to slidably receive one or more components of the modular applicator therethrough, such as, for example, a needle 300 (FIG. 1F).

Needle 300 may have a body 302 extending between a distal end 301 and a proximal end 303. The body 302 of needle 300 may be sized, shaped, and configured to be slidably received within respective inner channels of guide tube 600 and/or distal central conduit 110". It should be understood that a length of body 302 of needle 300 may be generally greater than a collective longitudinal length of guide tube 600 and distal central conduit 110". In this instance, distal end 301 of needle 300 may extend distally outward from distal opening 130 when needle 300 is received within the modular applicator. Needle 300 may be flexibly deformable such that body 302 and/or distal end 301 may deflect or otherwise conform to a configuration of inner channels of guide tube 600 and/or distal central conduit 110". For example, collar 120 may be angled relative to a proximal portion of distal central conduit 110", and body 302 of needle 300 may bend as is passes through distal central conduit 110'.

Due to an angular configuration of distal central conduit 110", inner channel 122" may be sized relatively greater than needle 300 to accommodate an outer diameter of needle 300 and a suitable clearance for needle 300 to bend within inner channel 122". By way of illustrative example, with distal central conduit 110" forming an angle of approximately 15 degrees between collar 120 and a proximal portion of distal central conduit 110", inner channel 122" may include a diameter of approximately 2.6 millimeters to accommodate needle 300 having a diameter of approximately 1.98 millimeters. In other examples, distal central conduit 110" may form an angle of approximately 30 degrees or approximately 45 degrees between collar 120 and a proximal portion of distal central conduit 110".

Distal central conduit 110" may include a slot 112 positioned along a proximal end of distal central conduit 110" opposite of collar 120 and may define an opening into distal central conduit 110". Slot 112 may be sized and shaped to receive the distal end of a guide tube 600. For example, slot 112 may have a shape that is complementary to a shape of the distal end of guide tube 600 and may include a snap-fit, friction-fit, screw-fit, bayonet-fit, or any other suitable type of connection for receiving the distal end of guide tube 600.

Guide tube 600 may include a body 602 extending between a distal end 604 and a proximal end 606 and an inner channel. The inner channel of guide tube 600 may be sized to receive, for example, needle 300 or a catheter, so that when guide tube 600 is connected to slot 112, the inner channel of guide tube 600 aligns with inner channel 122" of distal central conduit 110".

Slot 112 may include a coupling interface disposed therein that may be formed of one or more protrusions and/or recesses. In the example, guide tube 600 may include a corresponding coupling interface formed of one or more protrusions and/or recesses along distal end 604. Accordingly, slot 112 and distal end 604 of guide tube 600 may be configured to mate with one another via the respective coupling interfaces to securely couple guide tube 600 to distal central conduit 110". In the present example, distal end 604 of guide tube 600 may be laterally received into slot 112 to engage a corresponding coupling interface of slot 112. With distal end 604 received within and engaged to slot 112, body 602 of guide tube 600 may be axially fixed relative to distal central conduit 110". In this instance, an inner channel of guide tube 600 may be at least partially aligned with inner channel 122" of distal central conduit 110".

With guide tube 600 coupled to distal central conduit 110" at slot 112, needle 300 may be slidably received within elongated body 602 via an opening at proximal end 606. Needle 300 may be passed through an inner channel of guide tube 600 and received within inner channel 122" of distal central conduit 110". In some aspects, needle 300 may be configured to connect to guide tube 600 and/or distal central conduit 110" once positioned therein via any suitable mechanisms, including, for example, a snap-fit, friction-fit, screw-fit, or bayonet-fit. In other aspects, one or more of distal central conduit 110" and/or guide tube 600 may include a corresponding engagement mechanism for coupling needle 300 thereto. Needle 300 may include a lumen extending through body 302. With needle 300 received through distal central conduit 110", distal end 301 of needle 300 may extend distally from collar 120 via distal opening 130. It should be appreciated that a substance and/or material received in needle 300 (e.g., a radioactive source) may be dispensed to a position distal to distal opening 130.

As shown in FIGS. 2A-2C, one or more peripheral elements may be coupled to interstitial tube 100 via first connector 500. For example, first connector 500 may be configured to couple with portions of one or more ovoid tubes 200, such as one or more second connectors 250 of ovoid tubes 200, 200' (e.g., by snap-fit connection), and/or may couple directly with ovoid tubes 200, 200'. Various coupling mechanisms will be described further herein.

Figure 4:
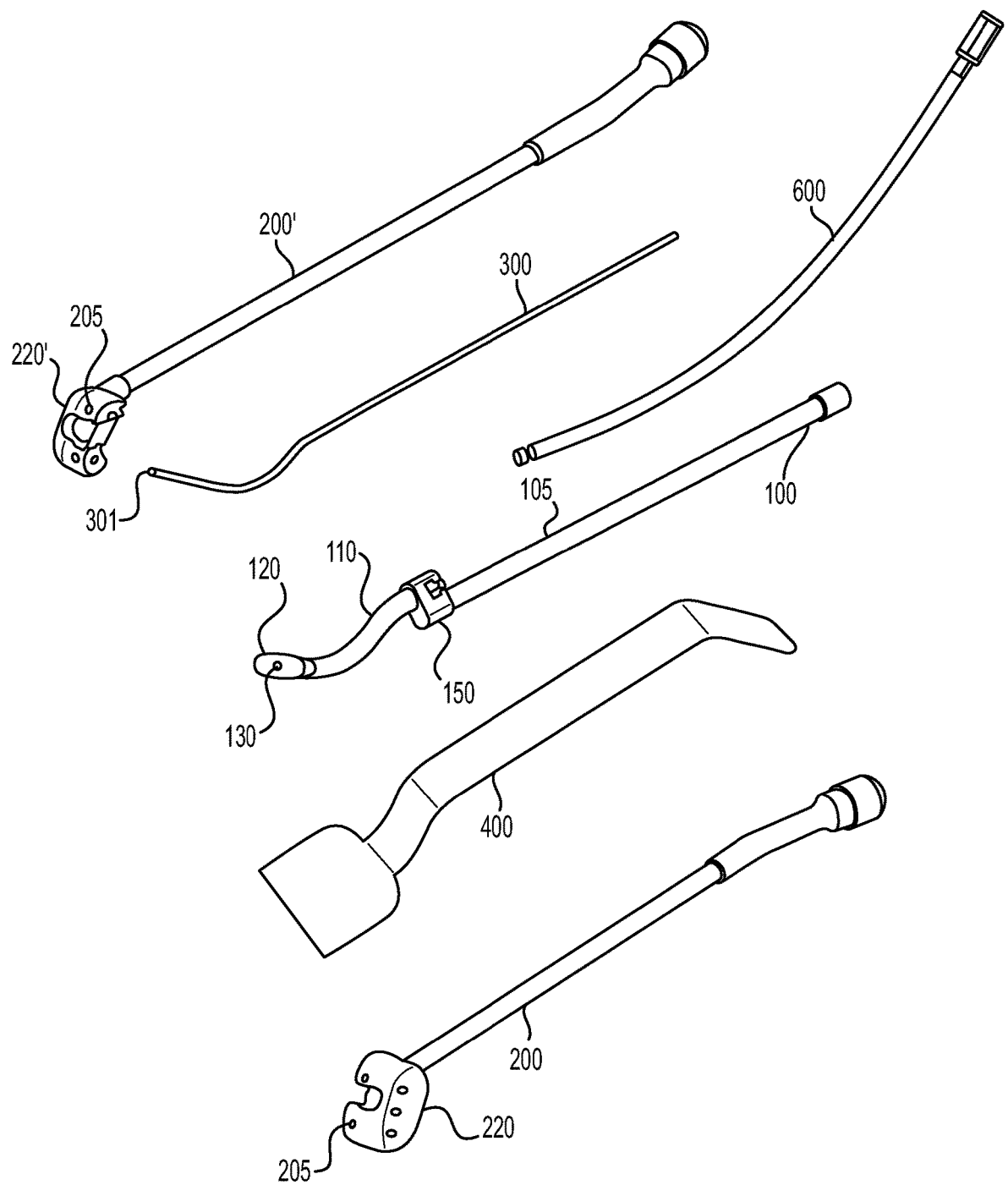
FIG. 4 is an exploded view of exemplary components of a modular applicator, according to one or more embodiments of the present disclosure.

One or more types of first connectors 500, 500' may be configured to couple interstitial tube 100 or IU tube 107 to one or more peripheral elements (e.g., one or more ovoid tubes 200, 200', guide tube 600, and/or rectal retractor 400) shown in FIG. 4. FIGS. 2A-2C and 3A-3C show various peripheral elements that may be coupled to interstitial tube 100 or IU tube 107 and will be described in further detail below. One or more first connectors 500, 500' (FIGS. 5 and 6) may include a central fixation bore 510 dimensioned to receive the main body 105 of interstitial tube 100 (or IU tube 107) within it. As shown in FIG. 1A, main body 105 of interstitial tube 100 (or IU tube 107) may pass through central fixation bore 510 so that first connector 500 (or 500') is positioned along a mid-region of interstitial tube 100.

Figure 5:
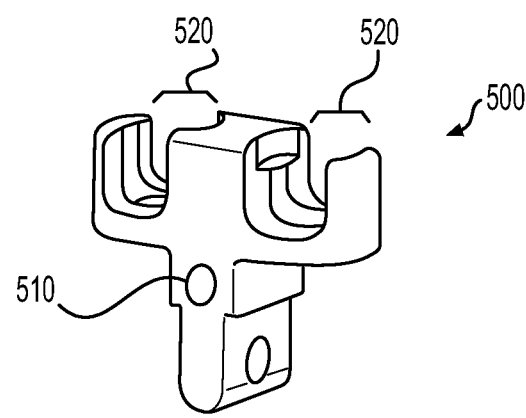
FIG. 5 is a perspective view of an exemplary first connector, according to one or more embodiments of the present disclosure.

In some embodiments, first connector 500, 500' may include one or more coupling cavities 520, 520' dimensioned to receive one or more ovoid tubes 200, 200'. In this manner, first connector 500, 500' may allow one or more ovoid tubes 200, 200', e.g., second connectors 250 of ovoid tubes 200, 200', to couple to interstitial tube 100. FIG. 5 depicts coupling cavities 520 on opposing sides of the central fixation bore 510 of first connector 500. The coupling cavities 520 may be configured to couple with portions of one or more ovoid tubes 200 (e.g., one or more second connectors 250 of ovoid tubes 200, 200', or directly with the ovoid tubes 200, 200' themselves) when a user pushes a portion of an ovoid tube 200, 200' down into each coupling cavity 520 from above. For example, coupling cavities 520 may engage with second connectors 250 (FIGS. 2A, 2C) to secure ovoid tubes 200, 200' to interstitial tube 100. First connector 500 may include two coupling cavities 520 for accommodating ovoid tubes 200, 200' (FIG. 5), or may additionally include a third (FIG. 1A) or fourth coupling cavity 520 to accommodate a guide tube 600 or transfer tube, for example.

Figure 6:
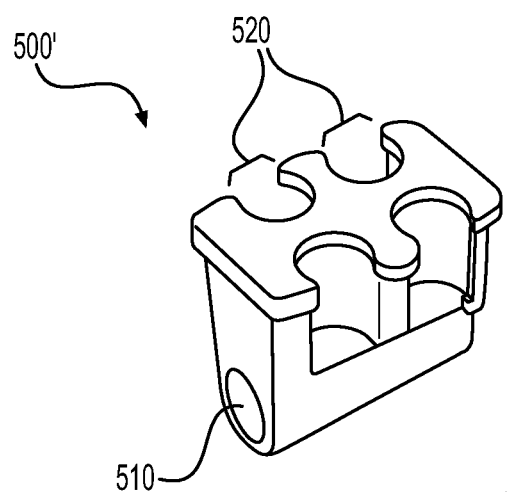
FIG. 6 is a perspective view of another exemplary first connector, according to one or more embodiments of the present disclosure.

FIG. 6 depicts a first connector 500' having a different arrangement of coupling cavities 520 and central fixation bore 510 than first connector 500 shown and described above in FIG. 5. The central fixation bore 510 may facilitate the coupling of first connector 500' to main body 105 of interstitial tube 100 (or IU tube 107), as described previously. Similarly, the coupling cavities 520 of first connector 500' may facilitate the coupling of first connector 500' to one or more peripheral elements (e.g., ovoid tube 200 and ovoid tube 200'). First connector 500' may include at least four coupling cavities 520 to allow for the connection of four peripheral members to interstitial tube 100 via first connector 500' or to allow attachment of one or two peripheral members (e.g., ovoid tubes 200, 200') at different optional locations. In other embodiments, fewer (e.g., two or three) or more (e.g., 5 to 10) coupling cavities may be included in first connector 500'. Coupling cavities 520 of first connectors 500, 500' may be oriented in different manners in order to allow ovoid tubes 200, 200' to mate with first connectors 500, 500' in different ways.

Figure 7A:
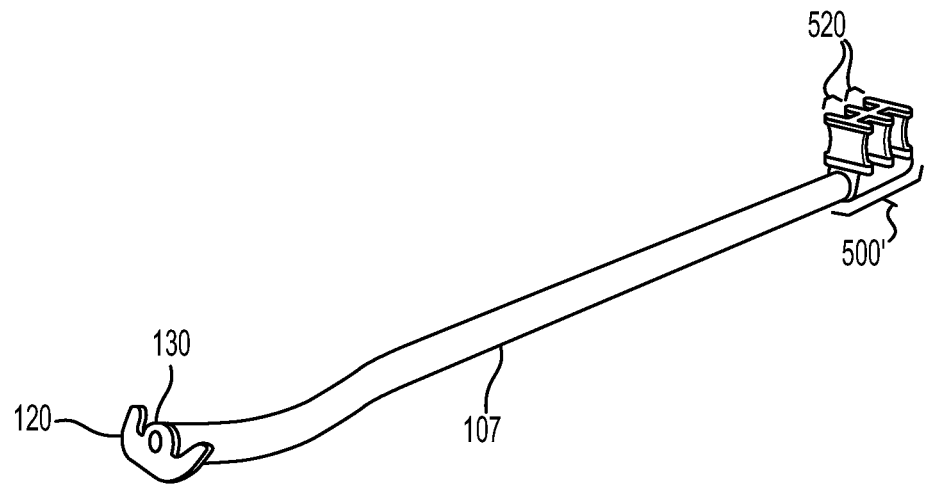
FIG. 7A is a perspective view of an IU tube including a first connector, according to one or more embodiments of the present disclosure.
Figure 7B:
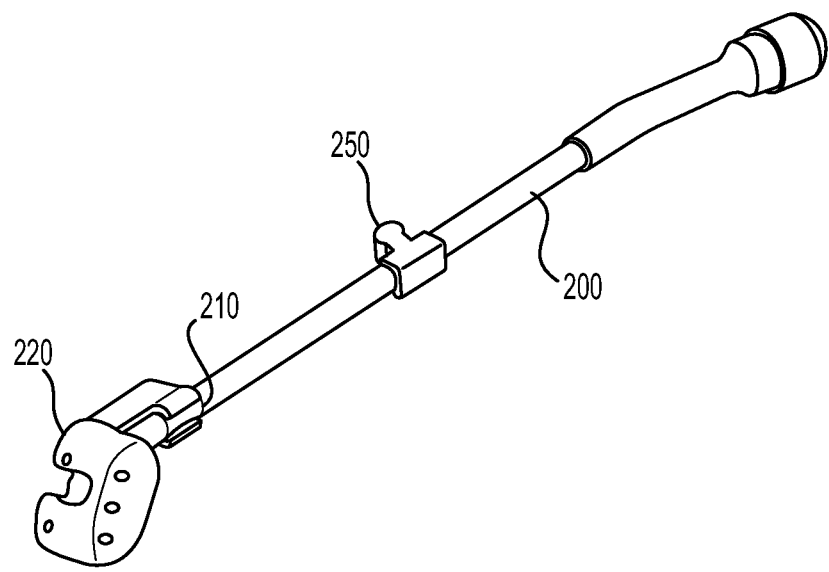
FIG. 7B is a perspective view of an ovoid tube including an ovoid and a second connector, according to one or more embodiments of the present disclosure.

For example, a coupling cavity 520 of first connector 500 (FIG. 5) may couple with a second connector 250 of ovoid tube 200 when the second connector 250 is moved (e.g., by pushing, sliding, snap-fitting, friction-fitting, clicking, or pressing) down into coupling cavity 520 from above, as in the embodiment of FIGS. 2A-2C. Coupling cavity 520 of first connector 500' (FIGS. 6, 7A, and 7B) may couple with a second connector 250 of ovoid tube 200 by moving (e.g., pushing, sliding, snap-fitting, friction-fitting, clicking, or pressing) second connector 250 laterally into coupling cavity 520. FIGS. 7A and 7B depict an IU tube 107 having a first connector 500' and an ovoid tube 200 uncoupled from one another. FIG. 8A shows second connector 250 of ovoid tube 200 about to couple with a coupling cavity 520, while FIG. 8B shows second connector 250 of ovoid tube 200 coupled to first connector 500'. In some embodiments, first connector 500' or ovoid tube 200 may include one or more anchors, hooks, clasps, or similar structures to secure second connector 250 and coupling cavities 520.

FIGS. 8C, 8D, and 9A-9C illustrate other exemplary first connectors 550, 550' that may be included as part of the modular applicator. Connector 550 may include body 551 that is configured to receive a main body of interstitial tube 100 or IU tube 107 therein to couple connector 550' to interstitial tube 100 or IU tube 107. Accordingly, connector 550 may facilitate coupling of one or more peripheral elements (e.g., one or more ovoid tubes 200, 200' (FIGS. 2A-2D) to interstitial tube 100 or IU tube 107, one or more guide tubes 600, and/or rectal retractor 400 (FIGS. 3A-3F)).

Connector 550 may include a central divider 552 and a pair of lateral flanges 554 extending laterally outward from central divider 552. Central divider 552 may extend outwardly (e.g., vertically upward) relative to body 551 and may be positioned between flanges 554.

Figure 2D:
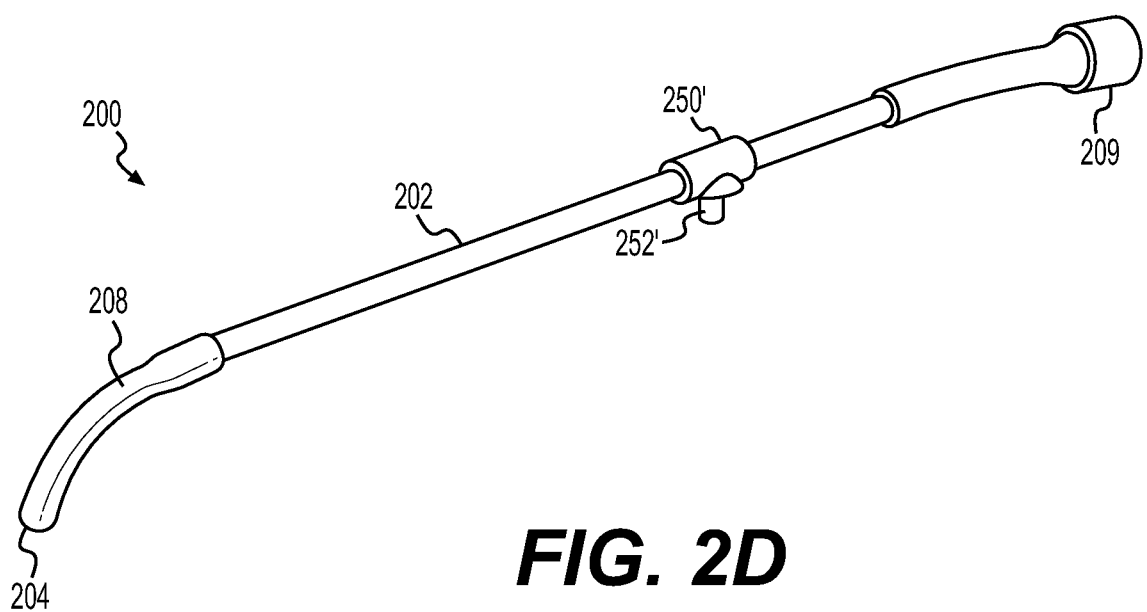
FIG. 2D is a perspective view of an exemplary ovoid tube, according to one or more embodiments of the present disclosure.

Referring now to FIG. 2D, in some embodiments, ovoid tube 200 may include second connector 250' coupled to a body 202 of ovoid tube 200, e.g., along an intermediate portion of between a proximal end 209 and a distal portion 208. Second connector 250' may be configured to couple ovoid tube 200 to first connector 550 (FIGS. 8C and 8D). Second connector 250' may include anchor 252' extending outwardly therefrom, with anchor 252' sized and shaped to be received within at least one of the apertures 556 of first connector 550 for securing ovoid tube 200 to interstitial tube 100 or IU tube 107.

As shown in FIGS. 8C-8D, ovoid tube 200 may be coupled to interstitial tube 100 by positioning second connector 250' along at least one of the lateral flanges 554 of connector 550 and inserting anchor 252' of second connector 250' into aperture 556 of lateral flange 554. In this manner, ovoid tube 200 may be secured to interstitial tube 100 or IU tube 107 via the engagement of connector 550 and second connector 250'. As described in greater detail below, ovoid tube 200 may be further secured to interstitial tube 100 or IU tube 107 along distal tip 204 via an engagement of distal central conduit 110' and ovoid 220, of which ovoid tube 200 may be securely coupled to as described further herein (see FIGS. 2F-2G).

Figure 9A:
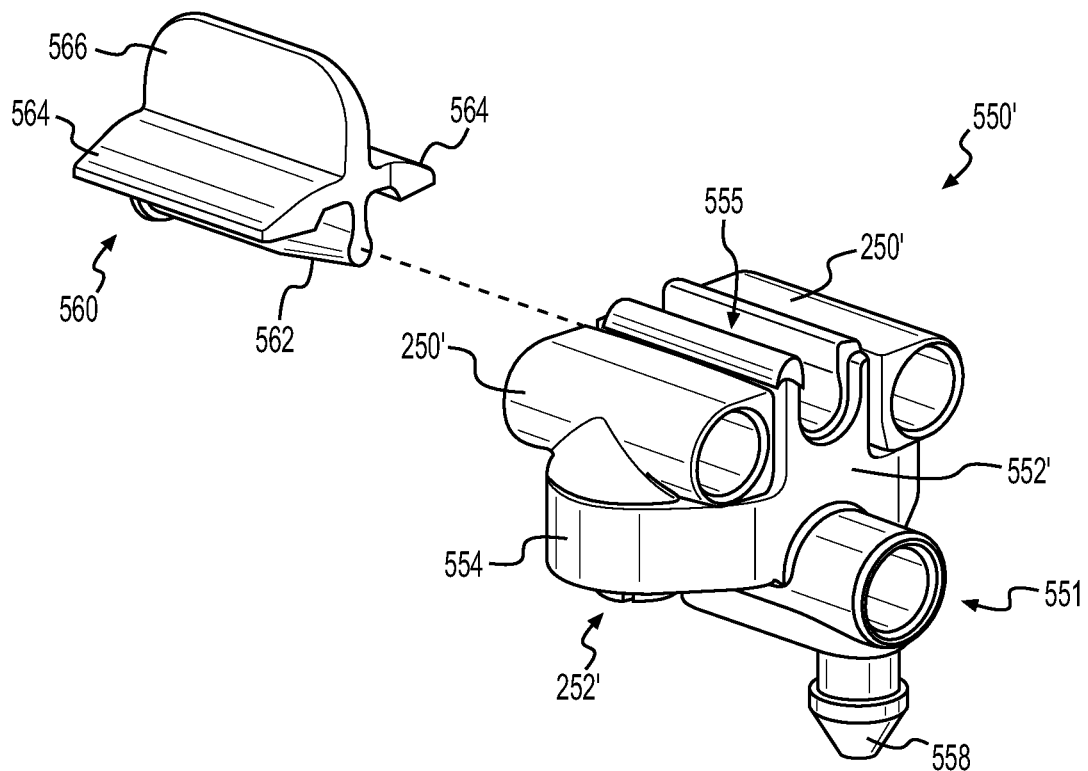
FIG. 9A is a perspective view of another exemplary first connector including a locking sled shown in an uncoupled state, according to one or more embodiments of the present disclosure.
Figure 9B:
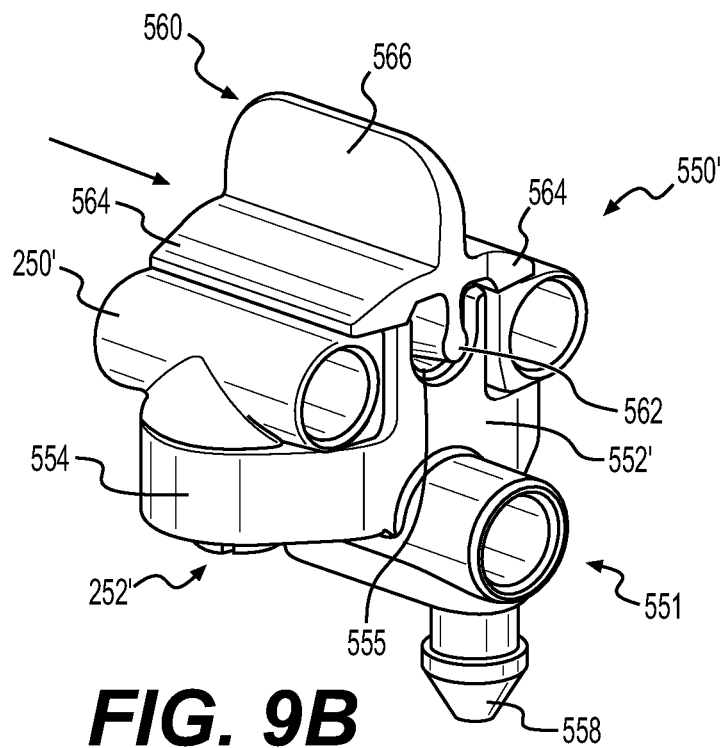
FIG. 9B is a perspective view of the first connector of FIG. 9A in a coupled state with the locking sled.
Figure 9C:
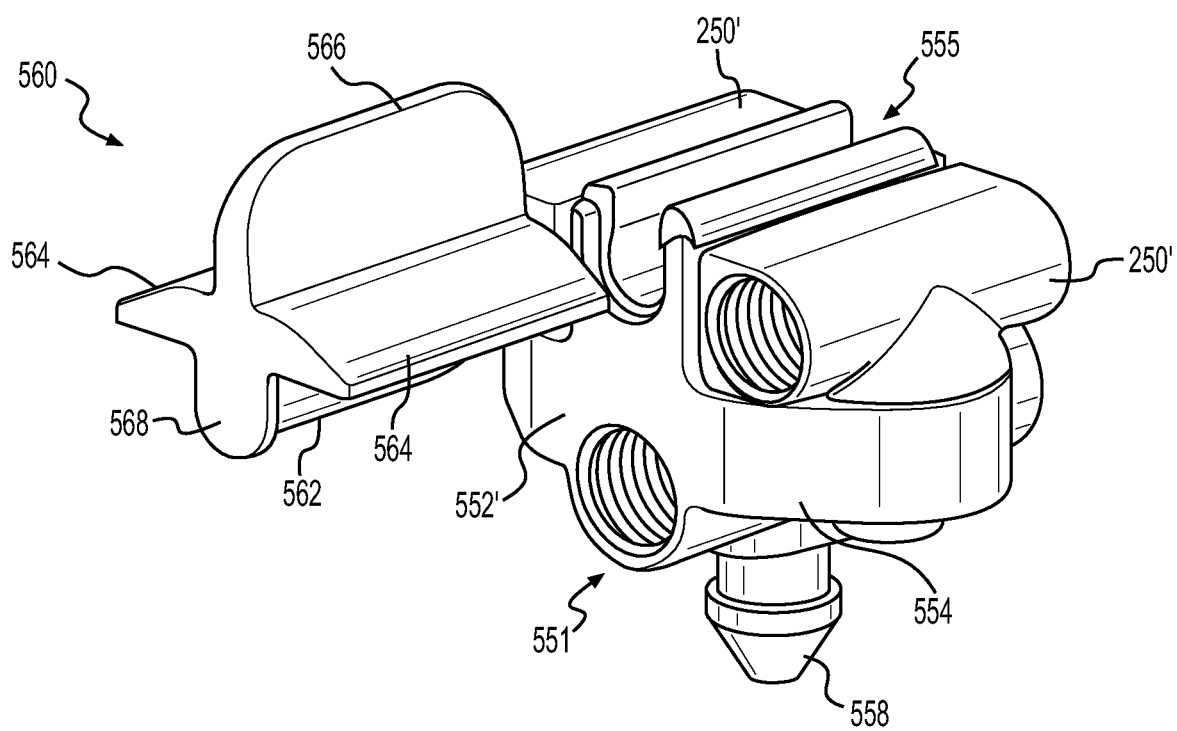
FIG. 9C is a perspective view of the first connector of FIG. 9A in a uncoupled state with the locking sled.

Referring now to FIGS. 9A-9C, in some embodiments, a first connector 550' may further include a locking mechanism in order to further secure ovoid tubes 200, 200' to first connector 550' once coupled. For example, central divider 552' may include a slot 555 disposed along a top surface of central divider 552' and disposed between the pair of flanges 554. Connector 550' may further include a removable sled 560 that is configured to slide in and out of slot 555 to engage body 551. For example, sled 560 may include a protrusion 562 configured to be received within slot 555 when sled 560 is slid into place to mate with slot 555. Although a sliding relationship between slot 555 and sled 560 is described herein, it is recognized that sled 560 may be snap-fit or otherwise coupled to slot 555. Sled 560 may further include a pair of lateral wings 564 and a handle 566. Handle 566 of sled 560 may define a surface that is configured to be graspable by a user of connector 550' to facilitate coupling and uncoupling of sled 560 with body 551 of first connector 550'.

Referring now to FIG. 9B, sled 560 is depicted in a coupled state with body 551 of first connector 550'. In this configuration, protrusion 562 is slidably received in slot 555 with lateral wings 564 disposed over second connectors 250' of attached ovoid tubes 200, 200' (not shown). By mating with first connector 550' in this manner, when second connectors 250' are received in flanges 554 of body 551 and coupled to first connector 550', sled 560 may be mated with body 551 to secure, fix, and/or lock second connectors 250' in place on first connector 550'. For example, lateral wings 564 engaging a top surface of second connectors 250' may lock second connectors 250' in place. Accordingly, sled 560 may prevent accidental displacement or dislodging of second connectors 250', and thus ovoid tubes 200, 200', relative to first connector 550' once a user has assembled these components of the applicator.

As shown in FIG. 9C, at least one terminal end of elongated protrusion 562 may include a widened section 568 that is sized and shaped relatively greater than an opening of slot 555. In other words, a lateral width of widened section 568 is greater than a width, diameter, and/or cross-sectional dimension of slot 555, as defined between the sidewalls of slot 555. Widened section 568 may be configured to engage the slot sidewalls in response to a translation of elongated protrusion 562 through slot 555. With widened section 568 of elongated protrusion 562 abutting against a terminal end of the sidewalls of slot 555, a position of sled 560 relative to body 551 may be fixed, thereby securing sled 560 to body 551 of connector 550'. Additionally and/or alternatively, as described above, sled 560 may form a snap-fit connection with body 551 of connector 550' in response to widened section 568 being at least partially received between or against a face of the sidewalls of slot 555. When snap-fit in place, an audible noise, e.g., a click, may be generated, or tactile feedback may be provided, to indicate to a user that sled 560 has been secured in place. Further, in some aspects, sled 560 may be slid into slot 555 of body 551 either from a proximal or distal direction by orienting widened section 568 away from slot 555 so that widened section 568 is the last portion of sled 560 to engage with slot 555 when slid into place.

In some embodiments, first connectors 500, 500', 550, 550' may be configured so that when ovoid tubes 200, 200' are connected to coupling cavities 520 (e.g., by second connectors 250, 250'), the angle of ovoid tubes 200, 200' may be adjustable relative to interstitial tube 100 or IU tube 107. In other embodiments, however, once ovoid tubes 200, 200' are coupled to interstitial tube 100 or IU tube 107, the positions and/or angles of the different parts may be fixed relative to one another and may not allow for movement of one or more of ovoid tubes 200, 200' and interstitial tube 100.

In some embodiments, second connectors 250, 250' of ovoid tubes 200, 200' may be able to slide along ovoid tubes 200, 200' to different positions on the ovoid tubes 200, 200'. Similarly, in some aspects first connectors 500, 500', 550, 550' may be configured to slide along main body 105 of interstitial tube 100 or IU tube 107 to adjust its displacement from collar 120. For example, FIG. 7A shows first connector 500' slid to a proximal position, and ovoid tube 200 may couple to first connector 500' when slid to any desired position along interstitial tube 100 or IU tube 107. This may further promote customization of exemplary applicators. In other embodiments, second connectors 250, 250' may be located at a fixed location on the ovoid tubes 200, 200' and/or first connectors 500, 500', 550, 550' may be coupled to interstitial tube 100 or IU tube 107 at a fixed location relative to collar 120.

The inclusion of first connectors 500, 500', 550, 550' and second connectors 250, 250' for connecting ovoid tubes 200, 200' to interstitial tube 100 or IU tube 107 may increase the usability of the modular applicators described herein. For example, the ability to, e.g., snap-fit, friction-fit, and/or click second connectors 250, 250' into first connectors 500, 500', 550, 550' to attach peripheral elements may reduce or eliminate the need for additional tools to assemble the applicators. In addition, first connectors 500, 500', 550, 550' may allow a user to assemble the applicator in any order. This is in contrast to many current applicators that may require additional tools or separate pieces, e.g., screws, screwdrivers, etc., to assemble the applicators and/or may require that certain pieces (e.g., the left or the right ovoid tube) be put together in a specific order. First connectors 500, 500', 550, 550' and/or second connectors 250, 250' may therefore facilitate the ease of use and customizability of applicators described herein.

As shown in FIGS. 2A-2C, ovoid tubes 200, 200' and/or ovoids 220, 220' may come in one of two orientations—a right-hand and a left-hand orientation (e.g., ovoid tube 200 and ovoid tube 200'). Each orientation may be configured to couple with a different lateral side of the first connector. Each ovoid tube 200, 200' may have an ovoid 220, 220' either removably or permanently associated with a distal region of the ovoid tube 200, 200'. When ovoid tubes 200, 200' are connected to a first connector, ovoids 220, 220' may be oriented around collar 120 of interstitial tube 100 or IU tube 107. For example, ovoid tube 200' may be configured to extend along the right side of interstitial tube 100 or IU tube 107, and an ovoid 220' associated with ovoid tube 200' may be configured to couple with the right side of collar 120. Ovoid tube 200 may be configured to extend along the left side of interstitial tube 100 or IU tube 107, and an ovoid 220 associated with ovoid tube 200 may be configured to couple with the left side of collar 120.

When ovoid tubes 200, 200' are connected to interstitial tube 100 or IU tube 107, ovoids 220, 220' may at least partially surround collar 120 and may fit together with one another and/or with collar 120. For example, ovoids 220 may snap-fit, friction-fit, bayonet-fit, or otherwise connect with one another and/or with collar 120. Where ovoids 220, 220' mate with each other, they may form a gap where collar 120 may be positioned (shown, e.g., in FIGS. 11A and 11B). As discussed in reference to FIGS. 1A-1C, 1E, and 1F, the distal tip of a catheter or needle 300 positioned within interstitial tube 100, may be configured to extend past the distal surface of collar 120. Accordingly, a distal region of any needle 300 or catheter, when positioned within interstitial tube 100, may extend distally of collar 120 and ovoids 220, 220'.

When ovoids 220, 220' are positioned around collar 120, they may cooperatively form a generally rectangular distally facing surface around collar 120. As used herein, the term "generally rectangular" means that the rectangular shape formed by ovoids 220, 220' may have rounded corners and/or rounded edges, as is shown in FIGS. 2A, 3A, and 11A-11B. Where the two halves of ovoids 220, 220' meet one another, they may form a smooth edge of the rectangle, or there may only be a slight depression where the two halves meet (as shown in FIGS. 11A, 11B, 12A, and 12B). In some embodiments, the lack of an indent or a gap between the top of the ovoids where they meet one another may inhibit tissue from bulging inward between the two ovoid halves. This may decrease the likelihood of over-treating tissue that bulges inward between the ovoids and may provide better visibility of the distal region of the applicator during use.

Figure 12A:
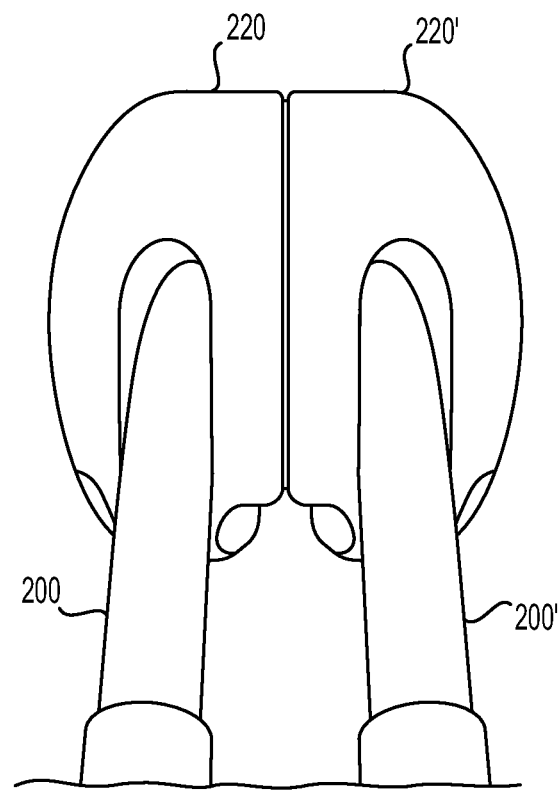
FIG. 12A is a rear view of two ovoid tubes including modular ovoids, according to one or more embodiments of the present disclosure.
Figure 12B:
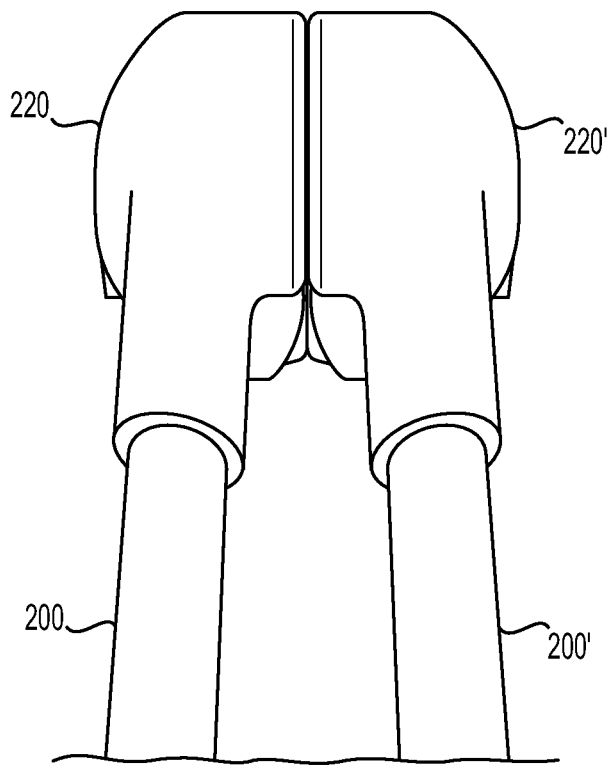
FIG. 12B is a rear view of two ovoid tubes including fixed ovoids, according to one or more embodiments of the present disclosure.

As shown in FIG. 2D, each ovoid tube 200, 200' may include a main body 202 having a generally tubular shape, although any cross-sectional shape may be suitable (e.g., oval, rectangular, etc.). In some embodiments, proximal end 209 of ovoid tubes 200, 200' may be key coded with one or more characters to provide proper connection of ovoid tube 200, 200' with an after-loading device for receiving a radioactive source therefrom. An ovoid 220 (FIG. 10C) may be coupled to the ovoid tube 200 (e.g., to the distal portion 208 of ovoid tube 200). The ovoid 220 may be permanently affixed to ovoid tube 200 (an example of which is shown in FIG. 12B) or may be configured to selectively couple and uncouple to ovoid tube 200 (an example of which is shown in FIG. 12A). For example, ovoid tube 200 may be configured to couple with different sizes or different shapes of ovoids 220 in a modular fashion in order to modify the applicator to accommodate different patient anatomies.

Figure 10A:
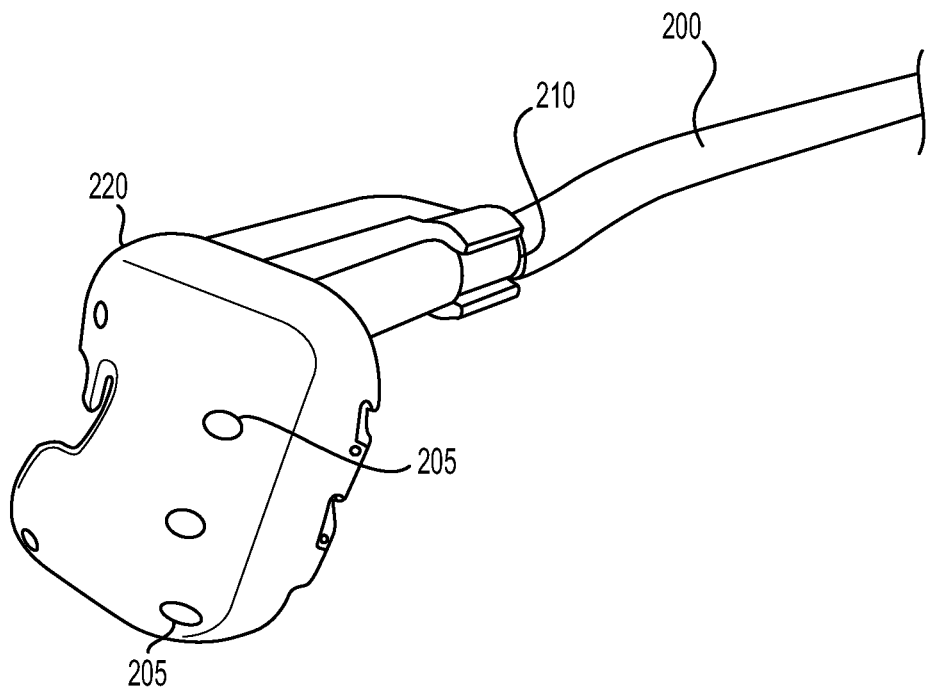
FIG. 10A is a perspective view of an ovoid tube including an ovoid, according to one or more embodiments of the present disclosure.
Figure 10B:
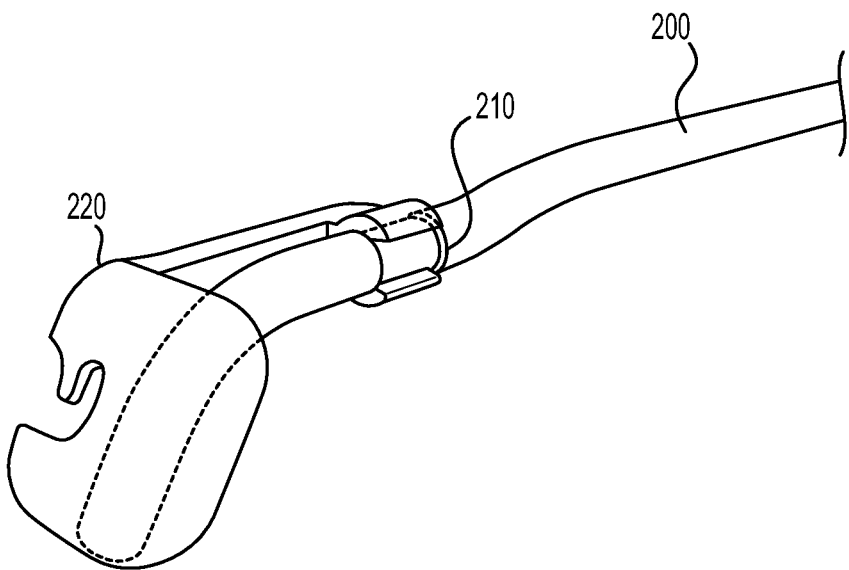
FIG. 10B is an internal view of an ovoid tube including an ovoid, according to one or more embodiments of the present disclosure.
Figure 10C:
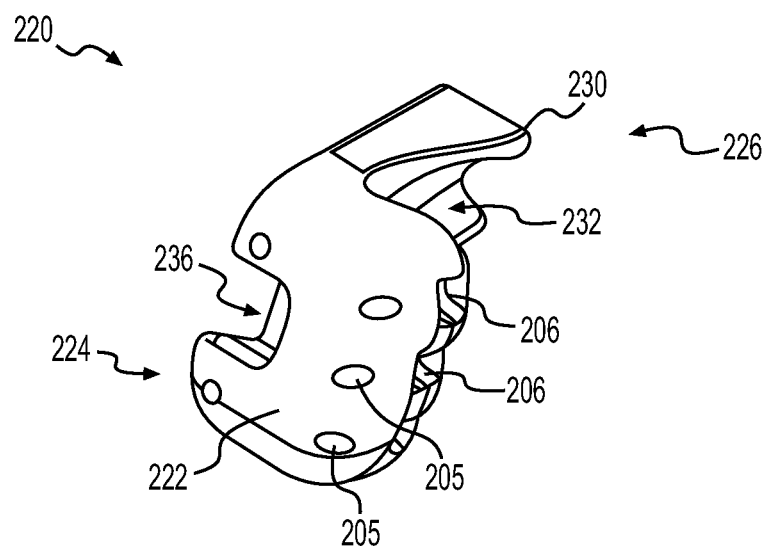
FIG. 10C is a perspective view of an exemplary ovoid, according to one or more embodiments of the present disclosure.

As shown in FIG. 10C, ovoid 220 may include a body 222 having a proximal portion 226 and a distal portion 224 that is positioned opposite of proximal portion 226. Body 222 of ovoid 220 may be formed of a generally rounded outer curvature so as to facilitate insertion into a subject. Each ovoid 220 may have one or more guide holes 205 and/or recesses 206 extending through body 222 of ovoid 220.

Each guide hole 205 of ovoid 220 may include a corresponding recess 206 for connecting a guide tube 600 with a proximal portion 226 of ovoid 220. Each guide hole 205 and recess 206 may be configured to allow a needle 300 or catheter configured to contain a radioactive source to pass through body 222, and more specifically, through a channel formed between guide tube 600 and guide hole 205 of ovoid 220. In some embodiments, due to a curvature of body 222, it should be appreciated that a longitudinal length of the channels formed between each guide hole 205 and corresponding recess 206 may be substantially similar to one another. In this instance, ovoid 220 may be configured and operable to maintain similar insertion depths for reaching a target treatment site with distal end 301 of needle 300 through each guide holes 205 on body 222. The inclusion of multiple guide holes 205 and recesses 206 may allow a user to position needles in numerous different places once the applicator is inserted into a subject in order to treat different areas of the subject's anatomy.

Recess 206 may be shaped and dimensioned to receive the distal end 604 of a guide tube 600, as discussed above. More particularly, recesses 206 on body 222 may be sized to receive needles 300 therethrough at varying angular orientations relative to a longitudinal axis defined between guide holes 205 and recess 206, such as, for example, angles ranging from about 0 degrees to about 15 degrees. During use, one or more guide tubes 600 may be connected to ovoids 220 to create a pathway through which a radioactive source may be passed from outside of a subject, through guide tubes 600, recesses 206, guide holes 205, and to target regions within the body of the subject.

Figure 11A:
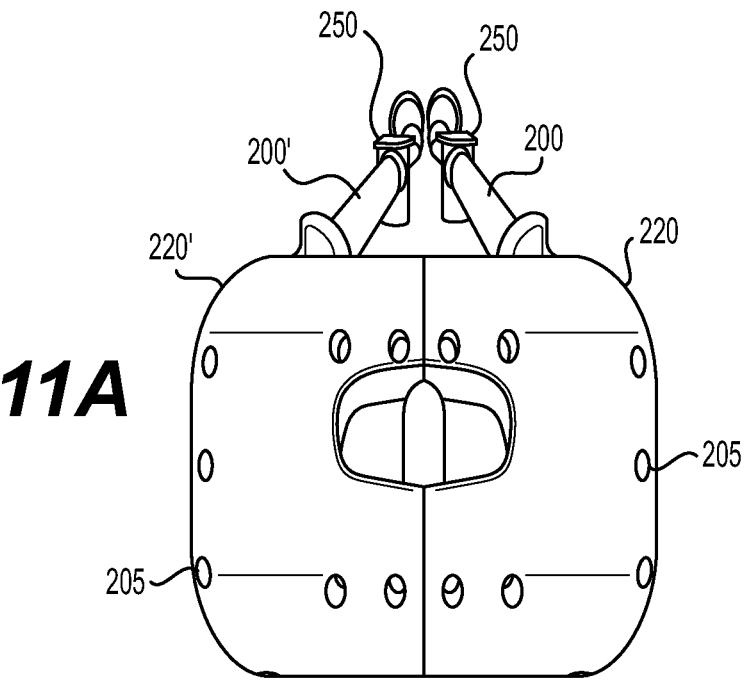
FIG. 11A is a pair of ovoid tubes and ovoids, according to one or more embodiments of the present disclosure.

Ovoids 220, 220' may include any suitable number of guide holes 205 and recesses 206, and/or any suitable arrangement of guide holes 205 and recesses 206 to allow for customization in positioning needles relative to the applicator to accommodate different patient anatomies and different treatment areas. In some embodiments, body 222 of ovoid 220 may include three guide holes 205 and three recesses 206, however, in other embodiments ovoid 220 may include additional and/or fewer guides holes 205 and recesses 206, respectively. Referring to FIG. 11A, for example, each ovoid 220, 220' may include seven guide holes 205 positioned at different radial positions relative to collar 120. In other embodiments, such as the example depicted in FIG. 11B, each ovoid 220, 220' may include five guide holes 205 positioned at different radial positions relative to collar 120. In other embodiments, each ovoid 220, 220' may include one, two, three, four, five, six, seven, eight, nine, ten, eleven, twelve, or more than twelve guide holes. In some embodiments, the number of guide holes 205 may depend, at least in part, on the size of ovoids 220, 220', while in other embodiments, the number of guide holes 205 may be independent of the size of 220, 220'.

Figure 11B:
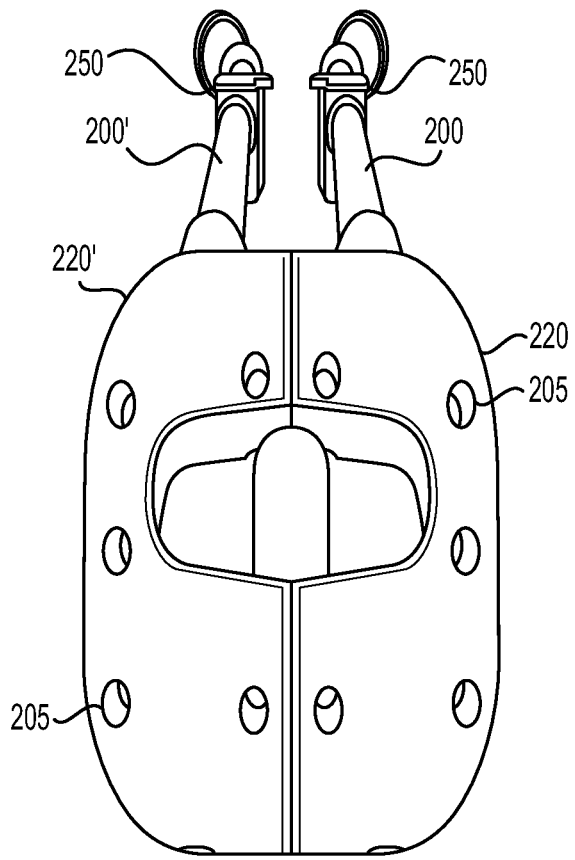
FIG. 11B is a perspective view of a pair of ovoid tubes and ovoids, according to one or more embodiments of the present disclosure.

As alluded to above, ovoids 220, 220' may come in different sizes in order to accommodate different patient anatomies. For example, some ethnicities, e.g., Asian ethnicities, may tend to have smaller anatomies than others. Accordingly, some ovoids 220, 220' (e.g., as shown in FIG. 11A) may have a larger width than other ovoids 220, 220' (e.g., as shown in FIG. 11B). Others may have a taller height or shorter height relative to one another. Exemplary ovoid sizes may be, e.g., 10-50 mm wide and 15-40 mm high. For example, individual ovoids may come in widths of 13, 15, 20, 25, 30, 35, or 40 mm and may be 30 mm in height or 25 mm in height. Exemplary ovoids may have a radius of 10 mm or 7.5 mm from a region where a source will be positioned to the surrounding tissue when positioned within a subject. For subjects with smaller anatomies, ovoids 220, 220' having smaller dimensions may be utilized with the modular applicator, such as those including a width of about 13 mm, a radius of about 7.5 mm, and/or a height of about 25 mm. As shown and described in further detail herein, a modular applicator may be configured to function with different ovoid sizes to allow the applicator to be customized to the anatomy of a specific subject.

Some exemplary ovoids may include a 13 mm wide by 25 mm high ovoid having three guide holes, a 15 mm wide by 30 mm high ovoid having three guide holes, a 20 mm wide by 30 mm high ovoid having five guide holes, a 25 mm wide by 30 mm high ovoid having five guide holes, a 30 mm wide by 30 mm high ovoid having five guide holes, a 35 mm wide by 30 mm high ovoid having seven guide holes, a 40 mm wide by 30 mm high ovoid having seven guide holes, or a 30 mm wide by 25 mm high ovoid having five guide holes, although this list of ovoid sizes is not exhaustive. Exemplary applicators disclosed herein may increase patient comfort, usability, and overall customizability by allowing a healthcare provider to select ovoids of different sizes for different subjects and to easily attach the selected ovoids to the device.

Accordingly, ovoid tubes 200, 200' may be configured to couple with (or may be permanently attached to) any size, shape, or configuration of ovoid 220. Referring to FIG. 10A, in some embodiments, ovoid 220 may include a proximal arm that extends along a side of ovoid tube 200 and couples to a recessed portion 210 of the ovoid tube 200. Each ovoid 220 may snap-fit and form a friction joint with recessed portion 210. Further, each ovoid 220 may be configured to couple with the collar 120 of interstitial tube 100. Referring to FIG. 10B, a distal portion of ovoid tube 200 may be received within an interior portion of ovoid 220 when coupled to ovoid 220.

The various attachments of ovoids 220, 220' to ovoid tubes 200, 200' may be removable to allow ovoids 220, 220' to couple and uncouple (e.g., click, snap, or otherwise friction-fit) to ovoid tubes 200, 200', or may be permanent so that ovoids 220, 220' are not intended to releasably couple and uncouple to ovoid tubes 200, 200'. In embodiments in which ovoids 220, 220' are removable and designed to snap, click, and/or otherwise friction-fit into place, no small parts and/or additional tooling may be needed to attach the ovoids to the ovoid tubes, as discussed above. This may increase ease of use and customizability compared to traditional applicators, which may require the use of multiple parts to assemble the ovoids or may require additional tooling. Alternatively, one or more screws may be used to attach ovoids 220, 220' to ovoid tubes 200, 200'.

Figure 10D:
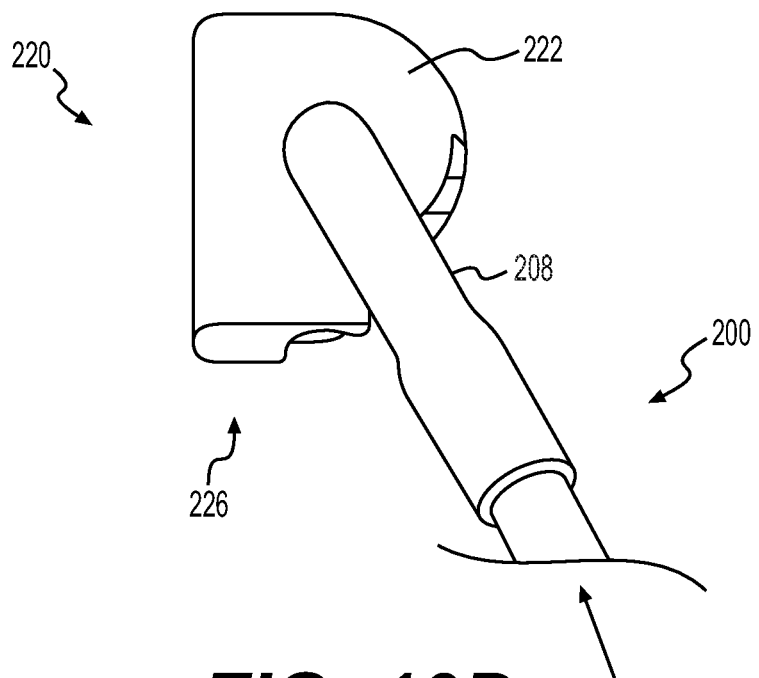
FIG. 10D is a rear view of the ovoid tube shown in FIG. 2D inserted into the ovoid shown in FIG. 10C.
Figure 10E:
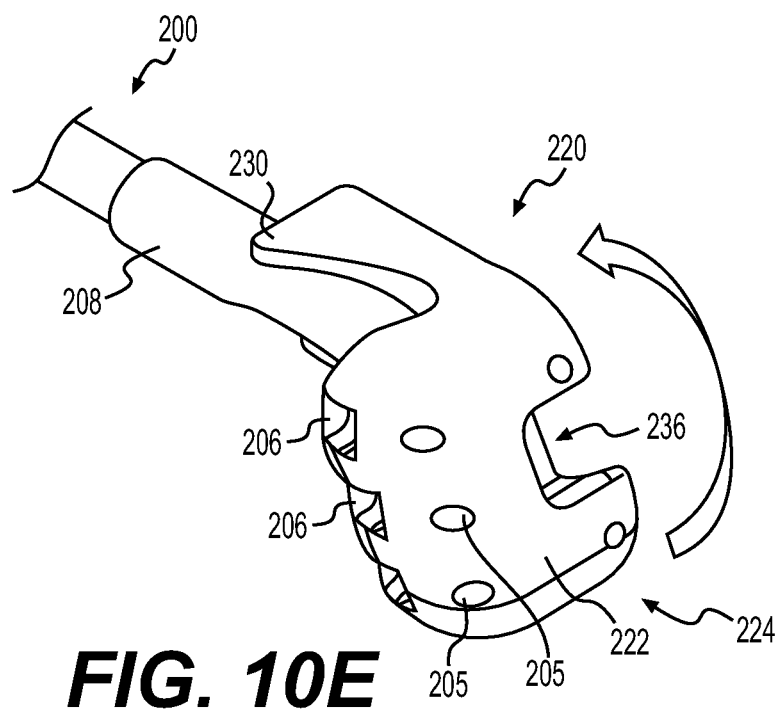
FIG. 10E is a perspective view of the ovoid tube shown in FIG. 2D coupled to the ovoid shown in FIG. 10C.

FIGS. 10C-10E depict another exemplary way in which avoid 220 may attach to ovoid tube 200. Ovoid 220 may include a proximal arm 230 that defines a channel 232. Channel 232 may be sized and shaped to correspond with a size and shape of distal portion 208 of ovoid tube 200 (FIG. 2D) to attach ovoid tube 200 to ovoid 220.

Referring now to FIG. 10D, in some aspects, coupling ovoid 220 to an ovoid tube 200 may include inserting distal tip 204 of ovoid tube 200 into a proximal opening in ovoid 220. When secured in place, distal portion 208 of ovoid tube 200 may be at least partially received within channel 232 of ovoid 220, while distal tip 204 is at least partially inserted within body 222 of ovoid 220. As shown in FIG. 10E, body 222 of ovoid 220 and/or ovoid tube 200 may be rotated (e.g., counterclockwise or clockwise) to couple ovoid tube 200 to ovoid 220. For example, upon rotation, distal portion 208 may be moved into alignment with channel 232 to securely couple ovoid 220 to ovoid tube 200. In other aspects, ovoid tube 200 and ovoid 220 may be snap-fit, friction fit, screwed, or otherwise secured in place relative to one another. With ovoid tube 200 coupled to ovoid 220, ovoid tube 200 may be inhibited from translating axially relative to channel 232.

Once ovoids 220, 220' are attached to ovoid tubes 200, 200', they may be positioned relative to one another so that ovoids 220, 220' couple (e.g., touch one another, couple to one another, or are otherwise aligned with one another), as is shown in FIGS. 11A and 11B. Once ovoid tubes 200, 200' are connected to interstitial tube 100 or IU tube 107, ovoids may be coupled with each other. Ovoids 220, 200' may also include one or more features to help them secure to and/or align with collar 120. For example, ovoids 220, 220' may further include a beveled recess 236 extending along one or more surfaces of ovoids 220, 220' configured to mate with collar 120 to secure and/or align ovoids 220, 220' to collar 120, as is shown further in 11C. Beveled recess 236 and/or collar 120 may include, e.g., one or more chamfers, protrusions, and/or recesses for securely grasping, guiding, and/or aligning at least a portion of collar 120 with beveled recesses 236. Beveled recesses 236 of ovoids 220, 220' may be configured to mechanically engage collar 120 therein, such as, for example, by a snap-fit, friction-fit, slide-fit, bayonet-fit, and/or any other suitable type of connection.

Figure 11C:
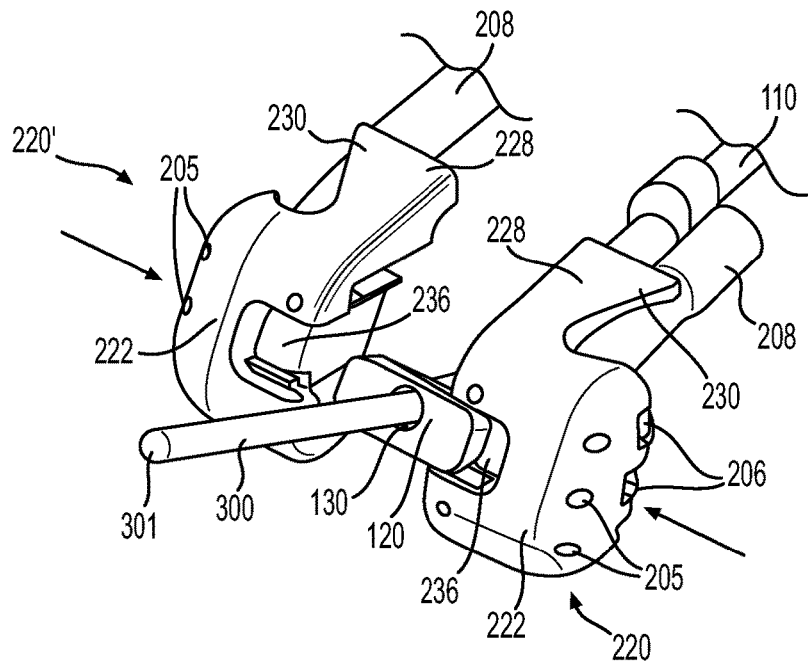
FIG. 11C is a perspective view of a pair of ovoids of an exemplary modular applicator in an uncoupled state, according to one or more embodiments of the present disclosure.

Referring to FIG. 11C, a pair of ovoids 220, 220' each having beveled recesses 236 may be positioned about opposing ends of collar 120 such that each of the opposing ends of collar 120 are at least partially received within one of the pair of beveled recesses 236 of ovoids 220, 220'. FIG. 11C shows ovoids 220, 220' being moved laterally into place around collar 120, as indicated by the inward-pointing arrows. While collar 120 may be configured to inhibit anterior and/or posterior movement of ovoids 220, 220' relative thereto once secured, in some aspects, a certain amount of lateral movement (referred to as spreading movement) of ovoids 220, 220' may be permitted. An exemplary applicator may include a mechanism that permits spreading of ovoids 220, 220' apart from one another and relative to collar 120. The amount of lateral spreading permitted may be up to about 5 millimeters for each ovoid 220, 220' (e.g., collectively up to about 10 millimeters). In some aspects, the amount of spreading permitted may depend, at least in part, on the size of ovoids 220, 220' used.

Figure 11D:
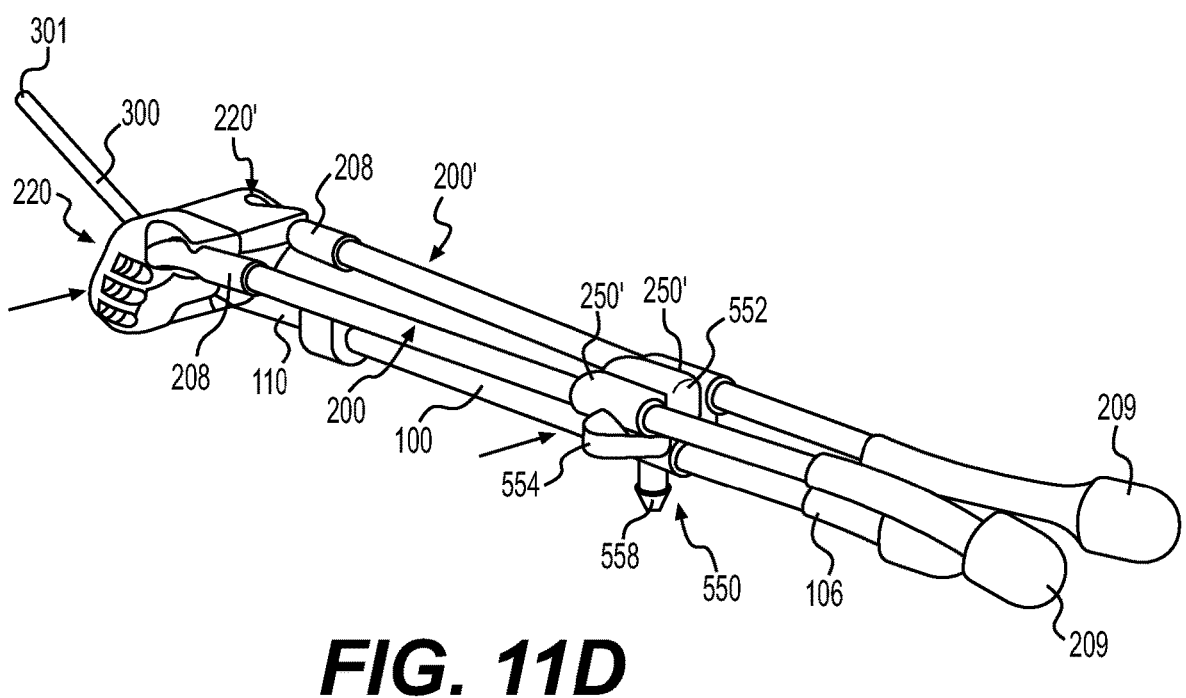
FIG. 11D is a perspective view of the modular applicator shown in FIG. 11C with the ovoids in a coupled state.
Figure 11E:
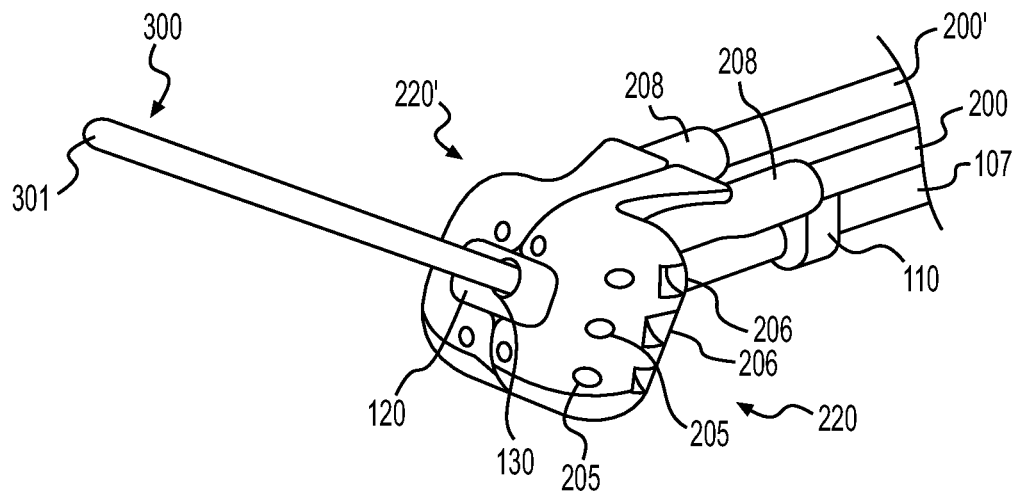
FIG. 11E is a perspective view of the pair of ovoids shown in FIG. 11C in a coupled state.

FIGS. 11D-11E depict collar 120 disposed between ovoids 220, 220'. With ovoids 220, 220' coupled to ovoid tubes 200, 200', ovoid tubes 200, 200' may be effectively secured to interstitial tube 100 via the engagement of beveled recesses 236 and collar 120 of distal central conduit 110. As shown in FIG. 11D, and as described in greater detail above, in addition to second connectors 250' of ovoid tubes 200, 200' engaging connector 550 of interstitial tube 100, a further engagement of ovoids 220, 220' with collar 120 may provide a second coupling point between ovoid tubes 200, 200' and interstitial tube 100 (or IU tube 107).

Figure 11F:
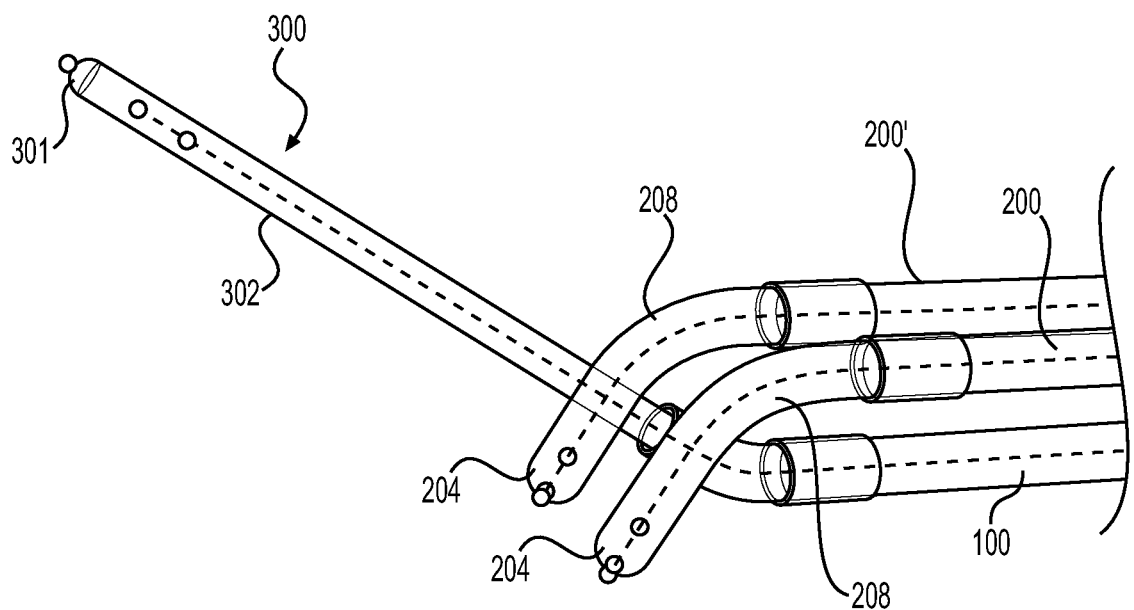
FIG. 11F is a partial perspective view of one or more travel paths of a radioactive seed within of the modular applicator shown in FIG. 11D, according to one or more embodiments of the present disclosure.

As shown in FIG. 11F, in addition to inserting a needle 300 through interstitial tube 100 to transmit a radioactive source to a target treatment site, in some embodiments, ovoid tubes 200, 200' may include internal lumens that may be configured to transmit a radioactive source therethrough.

With distal tip 204 of each ovoid tube 200, 200' disposed within body 222 of a respective ovoid 220, the internal lumen of each ovoid tube 200, 200' may extend into ovoids 220, 220' such that a radioactive source transmitted through ovoid tubes 200, 200' may be distributed to a target treatment site via ovoids 220, 220'.

Figure 13A:
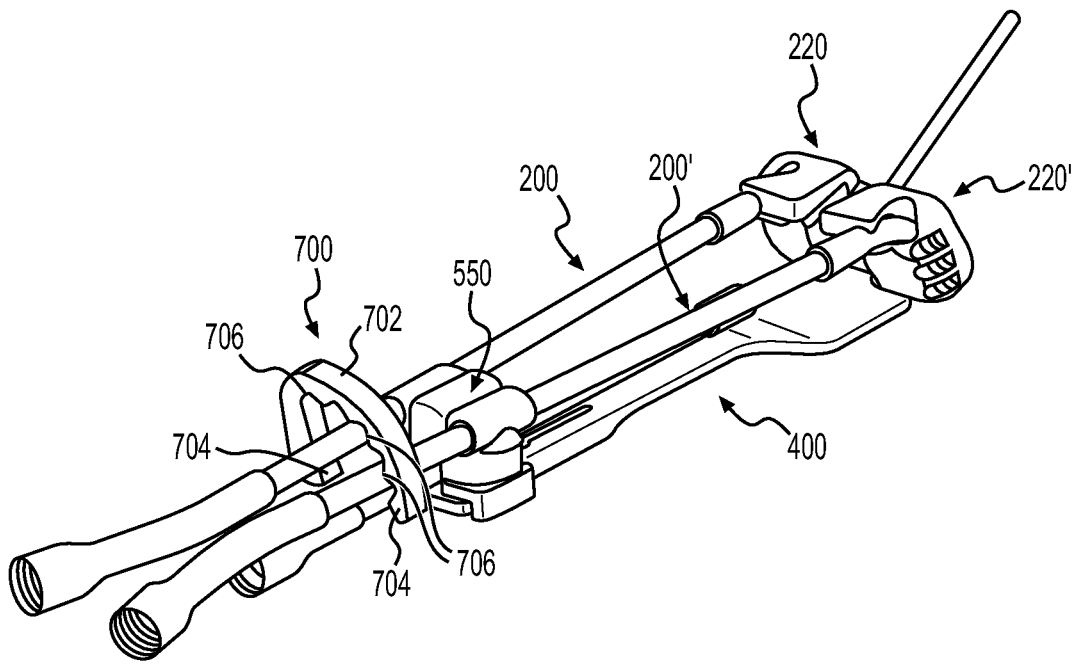
FIG. 13A is a perspective view of a modular applicator including an exemplary spreading clip in a separated state, according to one or more embodiments of the present disclosure.
Figure 13B:
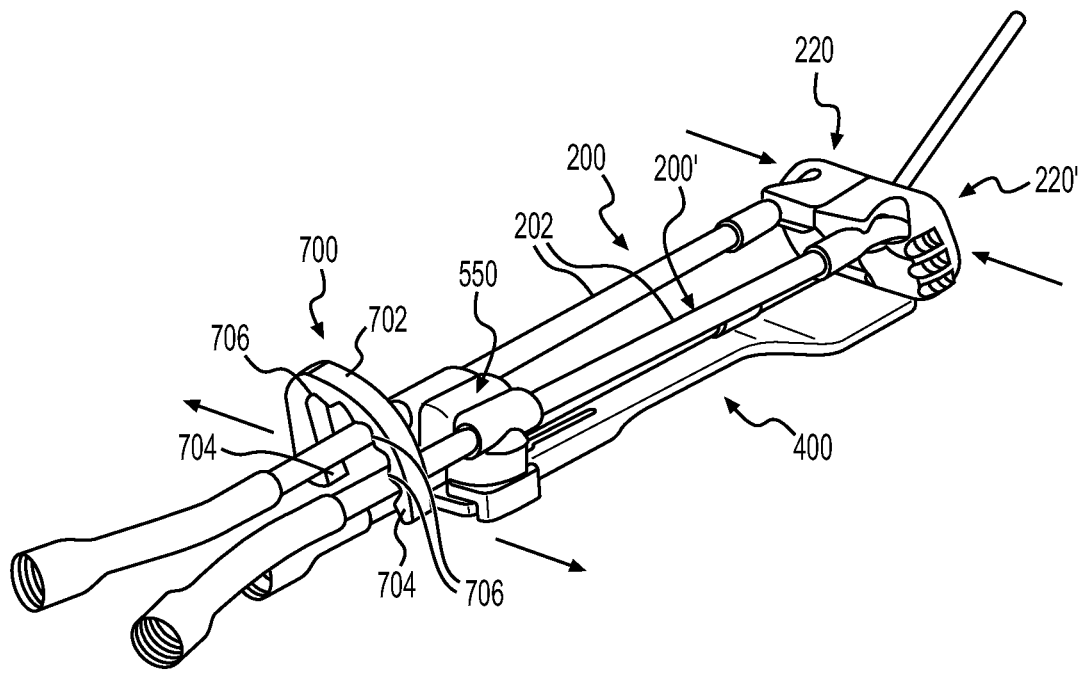
FIG. 13B is a perspective view of the modular applicator shown in FIG. 13A with the spreading clip in a contracted state.

Referring now to FIGS. 13A and 13B, in some uses of a modular applicator, it may be useful to move ovoids 220, 220' closer to one another or to move ovoids 220, 220' laterally away from one another to administer treatment. To achieve this function, a modular applicator may include a spreading clip configured to removably couple to a proximal region of ovoid tubes 200, 200' for selectively moving (e.g., spreading, contracting, and/or fixating) ovoid tubes 200, 200', and thus distally positioned ovoids 220, 220', relative to one another. Several examples of spreading clips are described herein, although other versions of spreading clips are also possible. Spreading clip 700 of FIGS. 13A and 13B may include a body 702 that is generally U-shaped and extends between opposing terminal ends 704. Spreading clip 700 may be sized such that ovoid tubes 200, 200', when assembled to first connector 550, may be received within U-shaped body 702.

Body 702 of spreading clip 700 may include a plurality of indentations 706 positioned along an interior surface of body 702 configured to engage with ovoid tubes 200, 200'. Indentations 706 may be integrally formed on body 702 or may be separate features secured to body 702. Further, in some embodiments, the plurality of indentations 706 may extend along a substantial length of body 702 between terminal ends 704, while in other embodiments, indentations 706 may be included along only a portion of body 702, e.g., along portions on opposing arms of the U-shaped body 702.

In some aspects, the spacing between individual indentations 706 may be regular or the spacing may change. For example, spacing between two or more indentations 706 positioned along opposing portions of the U-shaped body 702 may be generally greater adjacent to terminal ends 704 than along more medial portions of body 702.

Each indentation 706 may be sized and shaped to receive a portion of ovoid tube 200 or 200'. Body 702 of spreading clip 700 may be formed of one or more materials configured to inhibit flexible expansion and/or deformation of body 702 in response to an application of a force thereon, such as, for example, by ovoid tubes 200, 200' when received within spreading clip 700.

Referring to FIG. 13A, a modular applicator is depicted in a separated state with ovoids 220, 220' laterally spread apart relative to one another. In this state, collar 120 of interstitial tube 100 (or IU tube 107) may not be fully received within, and/or enclosed by, recesses 236 of ovoids 220, 220', as similarly shown in FIG. 11C. In this state, spreading clip 700 may be coupled to ovoid tubes 200, 200' such that ovoid tubes 200, 200' are received within indentations 706 of body 702 so that spreading clip 700 applies a first inward force to ovoid tubes 200, 200'. The force applied by spreading clip 700 may move the proximal ends of ovoid tubes 200, 200' closer together and thus may move the distal ends of ovoid tubes 200, 200'—and ovoid tubes ovoids 220, 220'—away from one another. The application of inward force by spreading clip 700 may cause ovoid tubes 200, 200' and second connectors 250' to rotate within aperture 756 of connector 550, thus allowing for lateral movement of the proximal and distal ends of ovoid tubes 200, 200'.

Referring now to FIG. 13B, ovoid tubes 200, 200' may be repositioned within respective indentations 706 of spreading clip 700 to apply a second inward force onto ovoid tubes 200, 200' that may be relatively less than the first inward force, or may apply no force to ovoid tubes 200, 200'. For example, ovoid tubes 200, 200' may be positioned within indentations 706 that may be relatively closer to terminal ends 704 of spreading clip 700. The relatively lesser second force (or application of no force) may allow ovoid tubes 200, 200' to move away from one another in a proximal region, thereby causing the distal ends of ovoid tubes 200, 200', and thus ovoids 220, 220', to move toward one another. Ovoids 220, 220' may move toward each other to decrease the amount of separation between them, e.g., so that there is no separation between the two ovoids and they contact one another. Because ovoid tubes 200, 200' may be fit into discrete indentations 706 of spreading clip 700 in order to control spreading of ovoids 220, 220', spreading clip 700 may allow incremental control over the position of ovoids 220, 220' relative to one another, as opposed to allowing for continuous control and movement of ovoids 220, 220'.

Figure 14A:
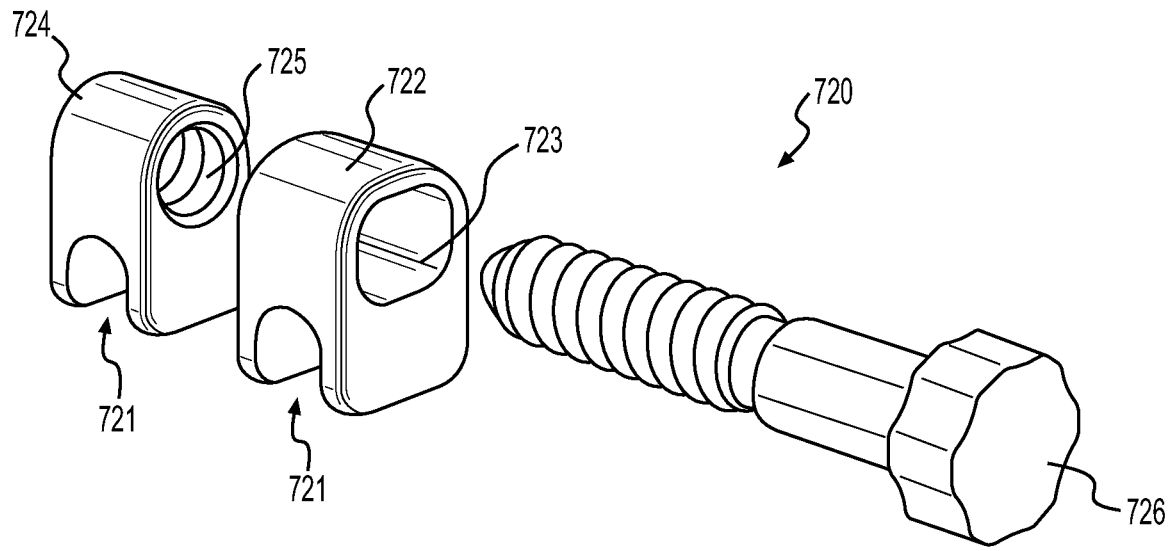
FIG. 14A is a perspective view of an exemplary spreading clip in a disassembled state, according to one or more embodiments of the present disclosure.
Figure 14B:
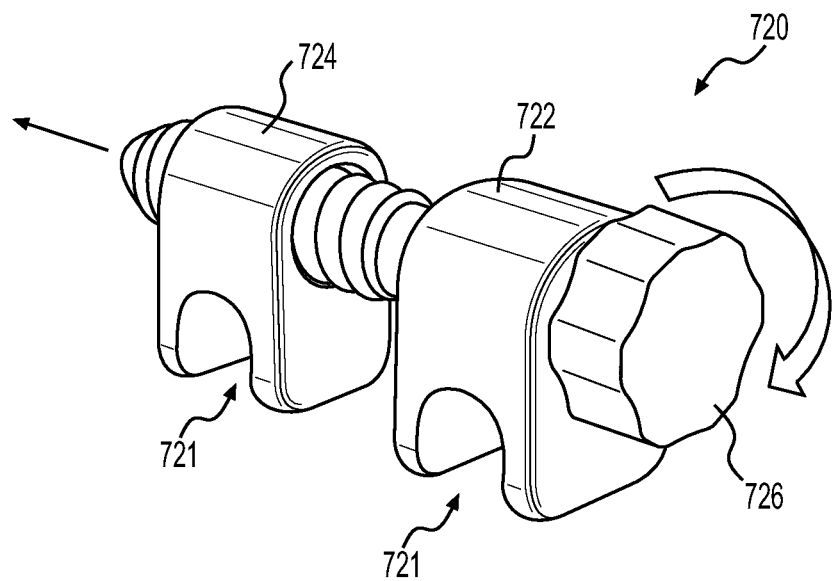
FIG. 14B is a perspective view of the spreading clip shown in FIG. 14A in an assembled state.

Another embodiment of a spreading clip is depicted in FIGS. 14A and 14B. Spreading clip 720 may allow for a continuous range of motion of ovoids 220, 220'. Spreading clip 720 may include three main parts: a first housing 722, a second housing 724, and a fastener 726. Referring initially to FIG. 14A, each of first and second housings 722, 724 include a slot 721 formed along a bottom surface of the respective first or second housing 722, 724. Slots 721 may be sized and shaped to receive at least a portion of either ovoid tube 200 or 200'. Each of housings 722, 724 may further include a channel 723, 725 extending therethrough. For example, first housing 722 may include a threaded or non-threaded channel 723 defining a flat interior surface, and second housing 724 may include a threaded-channel 725 defining an interior surface.

Channels 723, 725 may be sized, shaped, and configured to receive and/or engage at least a portion of fastener 726. Fastener 726 of spreading clip 720 may be a screw, for example. Fastener 726 may extend through first and second housings 722, 724 and, when rotated, may move first and second housings 722, 724 closer together or further apart from one another, depending on the direction of rotation. In this manner, when first and second housings 722, 724 are positioned to receive ovoid tubes 200, 200' in slots 721, respectively, rotation of fastener 726 may move ovoid tubes 200, 200' further apart from one another or closer to one another. As described above, movement of ovoid tubes 200, 200' closer together may cause ovoids 220, 220' to move apart from one another to a separated state, and movement of ovoid tubes 200, 200' apart from one another may cause ovoids 220, 220' to move closer together to one another to a contracted state.

Figure 15A:
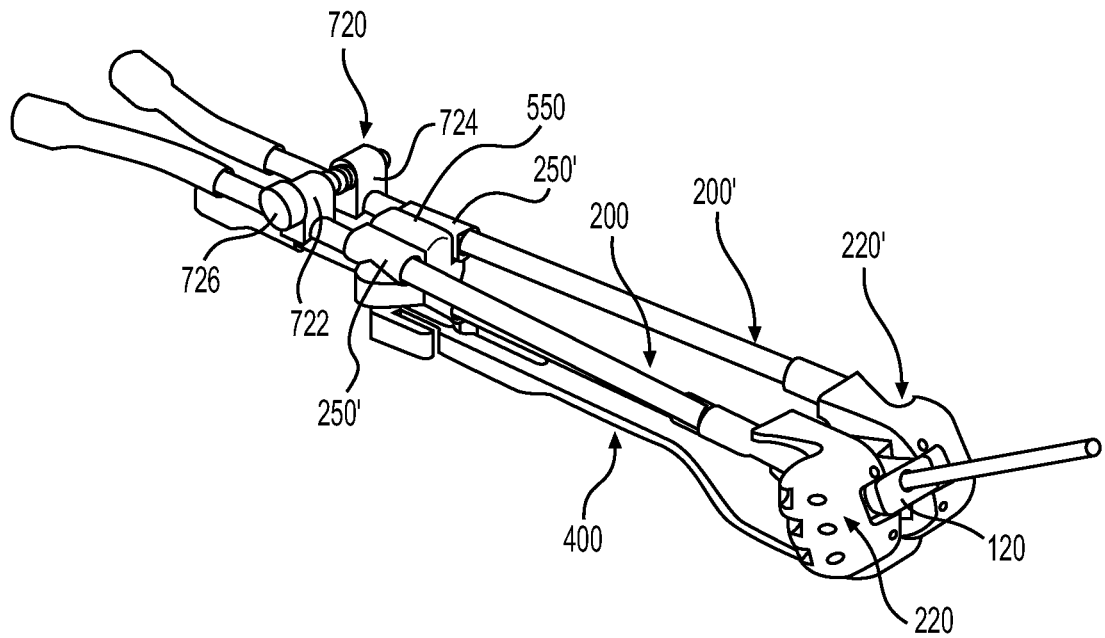
FIG. 15A is a perspective view of a modular applicator including the spreading clip of FIG. 14A, with the modular applicator in an separated state.
Figure 15B:
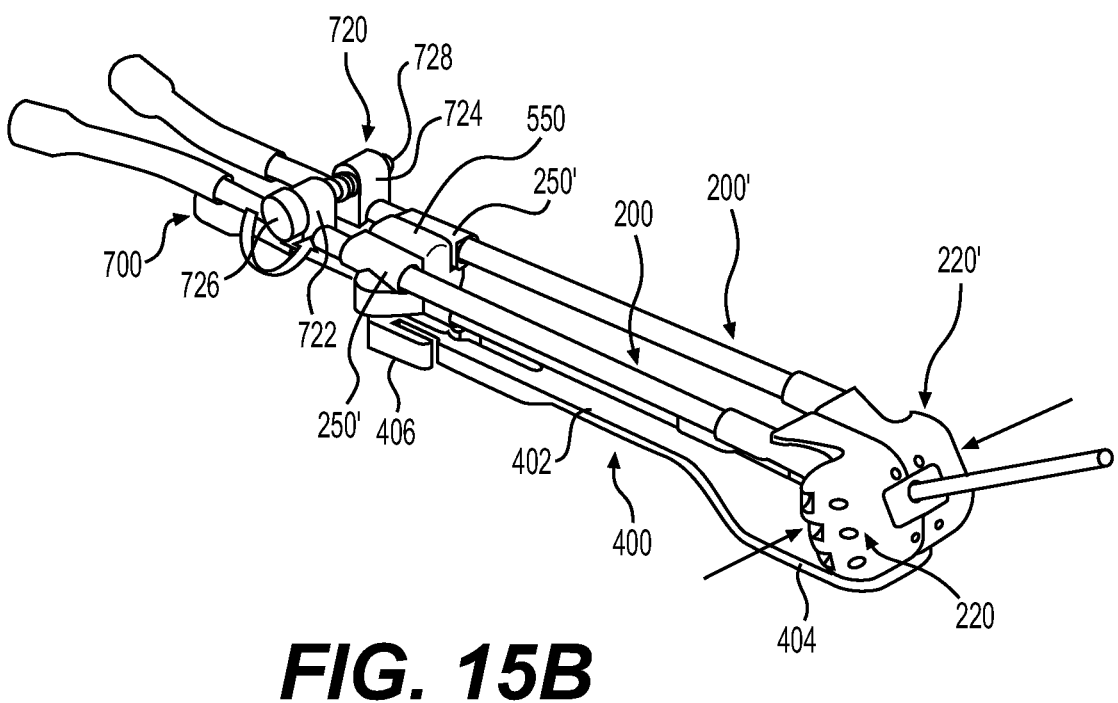
FIG. 15B is a perspective view of the modular applicator shown in FIG. 15A including the spreading clip of FIG. 14A, with the modular applicator in a contracted state.

FIGS. 15A-15B depict spreading clip 720 with the first and second housings 722, 724 coupled to ovoid tubes 200, 200' in the separated and contracted states. In FIG. 15A, the modular applicator is depicted in a separated state with ovoids 220, 220' separated from one another. In this instance, collar 120 is not fully received within, and/or enclosed by, the corresponding recesses 236 of ovoids 220, 220'. In FIG. 15A, fastener 726 has been rotated (in either a clockwise or counterclockwise direction) sufficiently enough to pull the pair of first and second housings 722, 724 towards each other, causing ovoid tubes 200, 200' attached to first and second housings 722, 724 to move toward one another. Continued rotation of fastener 726 may provide a continued translation of ovoid tube 200 toward ovoid tube 200', up until a maximum amount of spreading of ovoids 220, 220' has been reached.

Referring now to FIG. 15B, a modular applicator is depicted in a contracted state. To achieve a contracted state, fastener 726 may be rotated in an opposite direction (e.g., counterclockwise or clockwise) relative to how fastener 726 was rotated to achieve the configuration of 15A, releasing the force that had pulled first and second housings 722, 724 closer to one another, and allowing the first and second housings 722, 724—and thus ovoid tubes 200, 200'—to move away from one another, bringing ovoids 220, 220' closer together to one another. Translation of ovoids 220, 220' toward one another may position the modular applicator to a coupled state, with collar 120' enclosed between ovoids 220, 220'. It should be understood that, in other embodiments, ovoid tubes 200, 200' may be positioned within various other positions relative to one another in response to spreading clip 720 rotating and/or translating to a plurality of other extents than those shown and described herein.

Figure 16A:
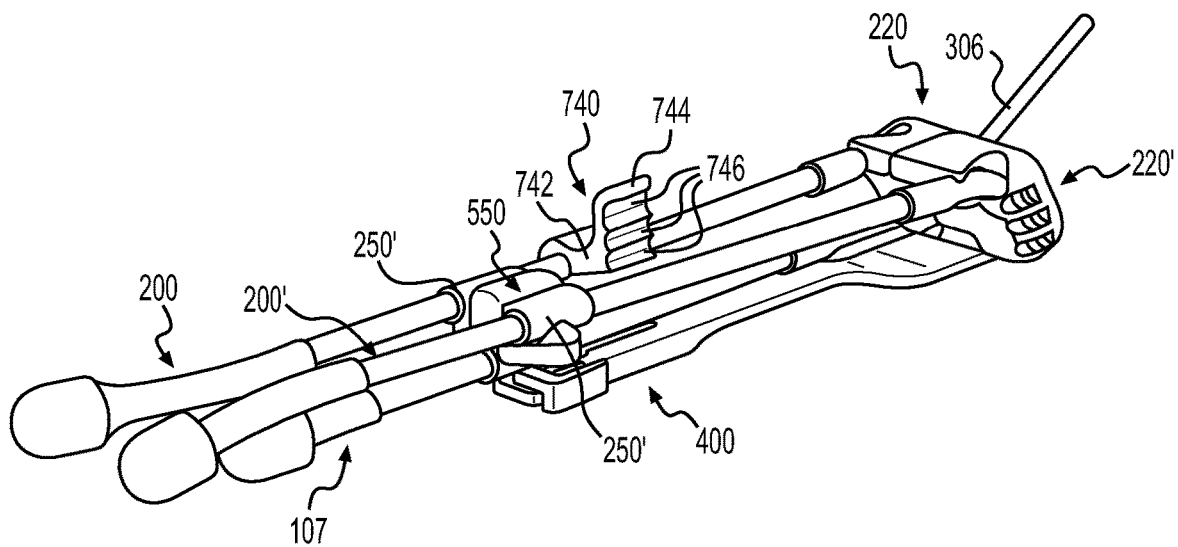
FIG. 16A is a perspective view of a modular applicator including an exemplary spreading clip in a disengaged state, according to one or more embodiments of the present disclosure.
Figure 16B:
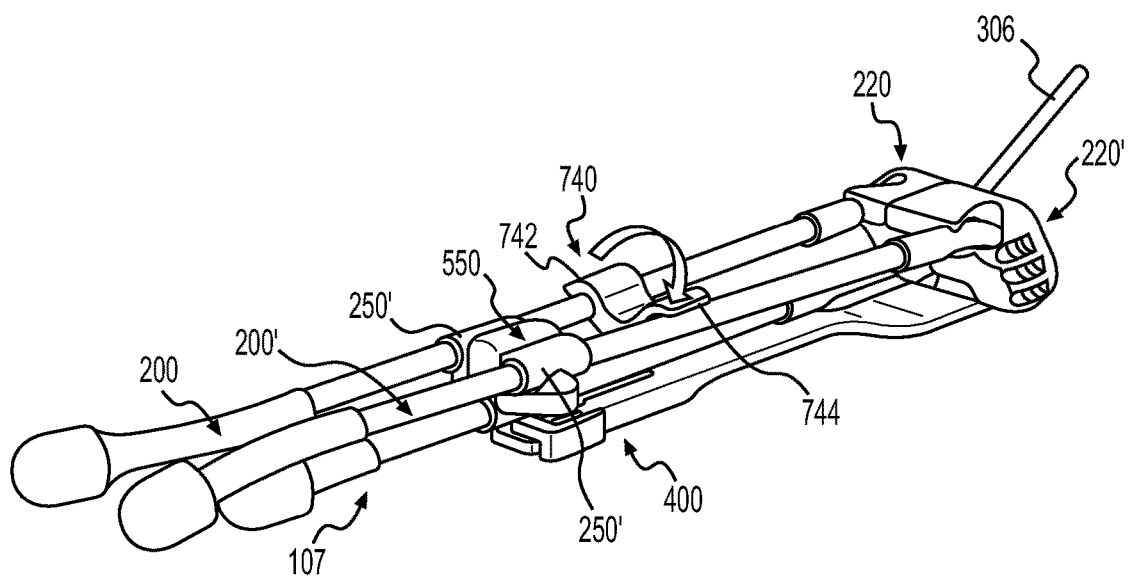
FIG. 16B is a perspective view of the modular applicator shown in FIG. 16A with the spreading clip in an engaged state.

Referring now to FIGS. 16A and 16B, in some embodiments, a modular applicator may include one or more spreading clips 740 coupled thereto for selectively moving ovoid tubes 200, 200', and thus ovoids 220, 220', relative to one another. Spreading clip 740 may include a movable body 742 secured to at least one of ovoid tubes 200, 200'. In particular, movable body 742 may be removably and/or pivotably coupled to at least one ovoid tube 200, 200'. Movable body 742 of spreading clip 740 may include an engagement arm 744 having a plurality of indentations 746 disposed along a surface configured to engage with an ovoid tube 200, 200'.

The plurality of indentations 746 extending along engagement arm 744 may be sized and shaped to at least partially receive an ovoid tube 200, 200'. Depending on which indentation 746 an ovoid tube 200, 200' is received within, ovoid tubes 200, 200' may be pulled closer to or farther apart from one another, moving ovoids 220, 200' farther apart or closer to one another. Accordingly, like spreading clip 700 of FIGS. 13A, 13B, spreading clip 740 may be used to move ovoid tubes 200, 200' and ovoids 220, 220' relative to each other at discrete intervals.

It should also be noted that spreading clips 700, 720, or 740 may be positioned proximal to first connector 500, 500', 550, 550' (as is shown in FIGS. 13A, 13B, 15A, 15B), or may be positioned distal to the first connector (as is shown in FIGS. 16A, 16B). In fact, spreading of ovoids 220, 220' may also be controlled by moving spreading clips 700, 720, or 740 proximally or distally along ovoid tubes 200, 200'.

When inserting a modular applicator of the disclosure into a person, interstitial tube 100 or IU tube 107 may first be positioned within the subject. After interstitial tube 100 or IU tube 107 is inserted into a subject (e.g., into the cervix of the subject in the case of IU tube 107 or a location of where the cervix would otherwise have been in the case of interstitial tube 100), ovoids 220, 220' may be inserted into the subject and attached to collar 120 using one or more spreading clips coupled to ovoid tubes 200, 200'. In other embodiments, to ease insertion procedures, at least one of ovoids 220, 200' may be preassembled onto collar 120 of interstitial tube 100 or IU tube 107 to prevent shifting of interstitial tube 100 or IU tube 107 within a patient.

Figure 17:
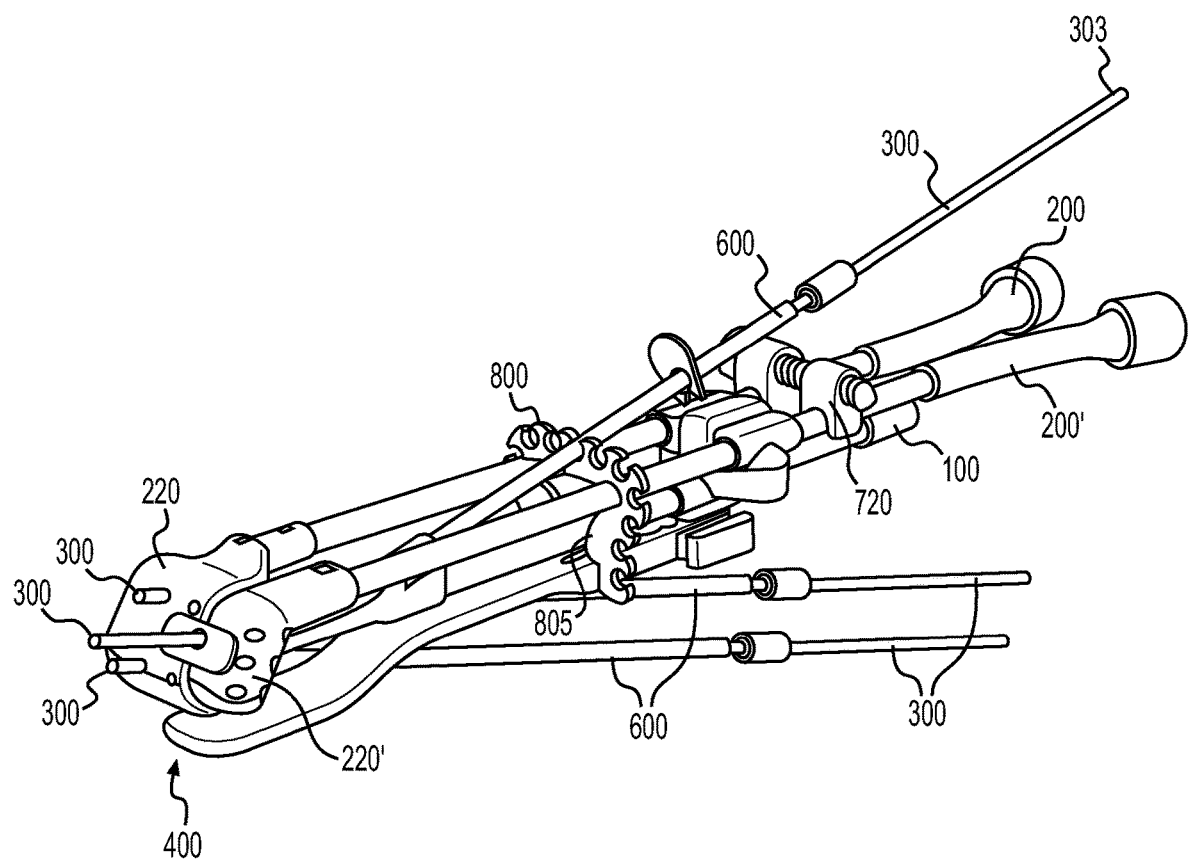
FIG. 17 is a perspective view of a modular applicator including a bracelet device.
Figure 18:
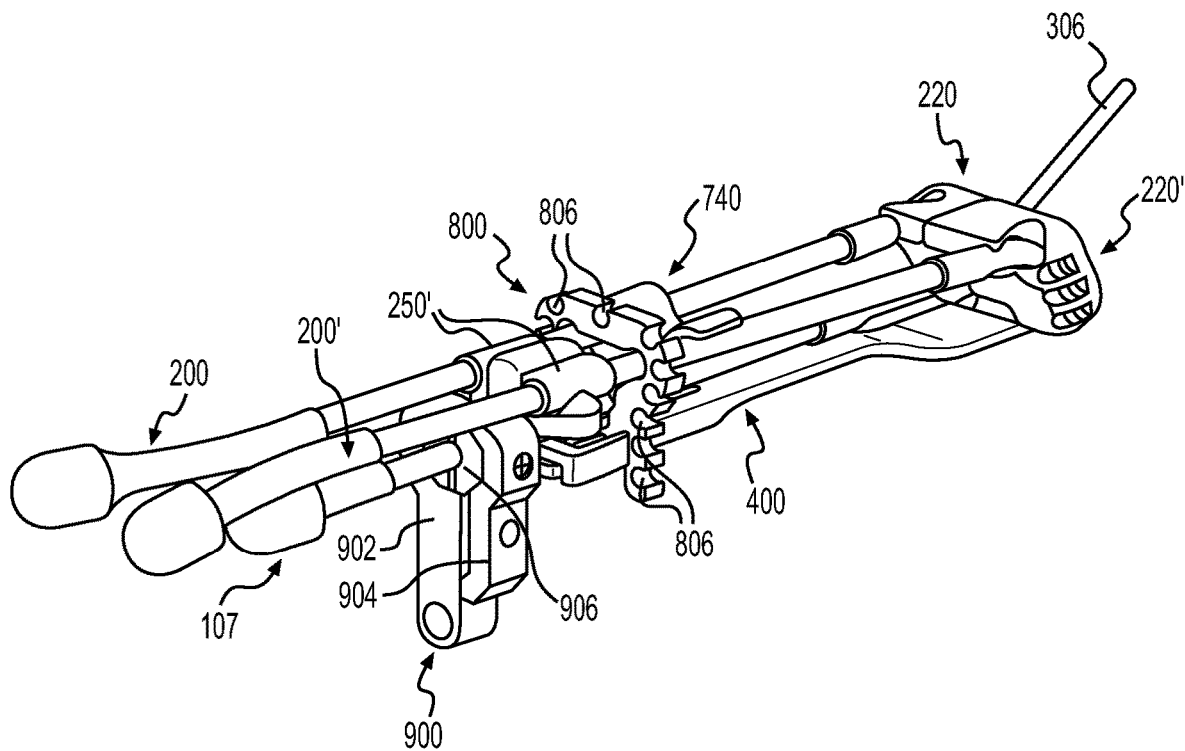
FIG. 18 is a perspective view of the modular applicator shown in FIG. 17 with a clamp assembly coupled thereto.

FIGS. 17-20 show other exemplary accessories that may be used with the modular applicators described in the current disclosure, as well as different configurations. Referring to FIG. 18, a bracelet device 800 configured and operable to couple with a modular applicator is depicted. Bracelet device 800 may be configured to hold one or more needles 300 relative to modular applicator during a procedure. Bracelet device 800 may be configured to engage ovoid tubes 200, 200' and/or interstitial tube 100 or IU tube 107 to thereby couple bracelet device 800 to the modular applicator. For example, bracelet device 800 may attach to ovoid tubes 200, 200' by a snap-fit connection and may include one or more protruding features 805 along an interior surface configured to snap onto ovoid tubes 200, 200' to securely couple ovoid tubes 200, 200'.

Body 802 of bracelet device 800 may include a plurality of slots or indents 806 positioned along an exterior surface into which one or more peripheral elements, such as, for example, needle 300, guide tube 600, etc., may be at least partially received. Accordingly, bracelet device 800 may be configured to fixate and/or sort one or more peripheral elements relative to the modular applicator during use and/or to provide an organized and clear overview of the peripheral elements in use during a procedure. For example, as shown in FIG. 17, guide tube 600 may be slidably received within one of the plurality of slots 806 of bracelet device 800, with needle 300 disposed within an inner lumen of guide tube 600.

Referring now to FIG. 18, in some embodiments, a modular applicator may be used with a clamp assembly 900 configured to immobilize a modular applicator relative to a patient during a procedure. This exemplary clamp assembly 900 may include a first clamp 902, a second clamp 904, and a pair of clamp inserts 906. Clamp assembly 900 may be configured to form a snap-fit connection with the modular applicator. In particular, clamp inserts 906 of clamp assembly 900 may be sized and shaped to couple about interstitial tube 100. In this instance, clamp inserts 906 are received about interstitial tube 100 or IU tube 107 along a region of an interstitial tube 100 or an IU tube 107 adjacent to proximal end 106. First clamp 902 and second clamp 904 may be disposed about clamp insert 906 to thereby enclose clamp insert 906 therebetween.

In other aspects, clamp assembly 900 may be coupled along other portions of interstitial tube 100 or IU tube 107 and/or to various other components of modular applicators of the current disclosure without departing from a scope of the present disclosure.

Figure 19:
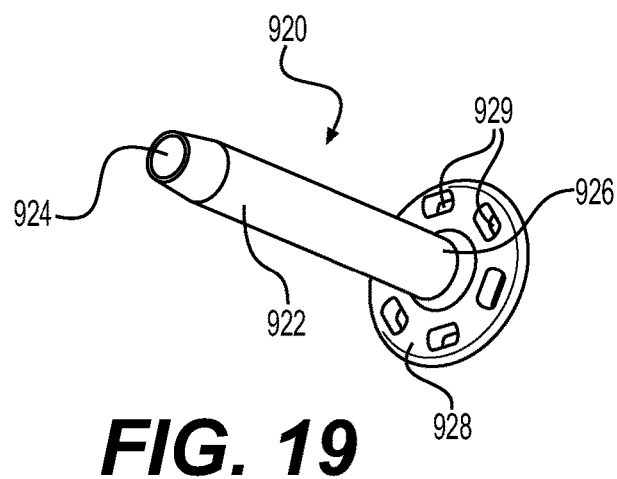
FIG. 19 is a perspective view of a sleeve for use with a modular applicator according to one or more embodiments of the present disclosure.
Figure 20:
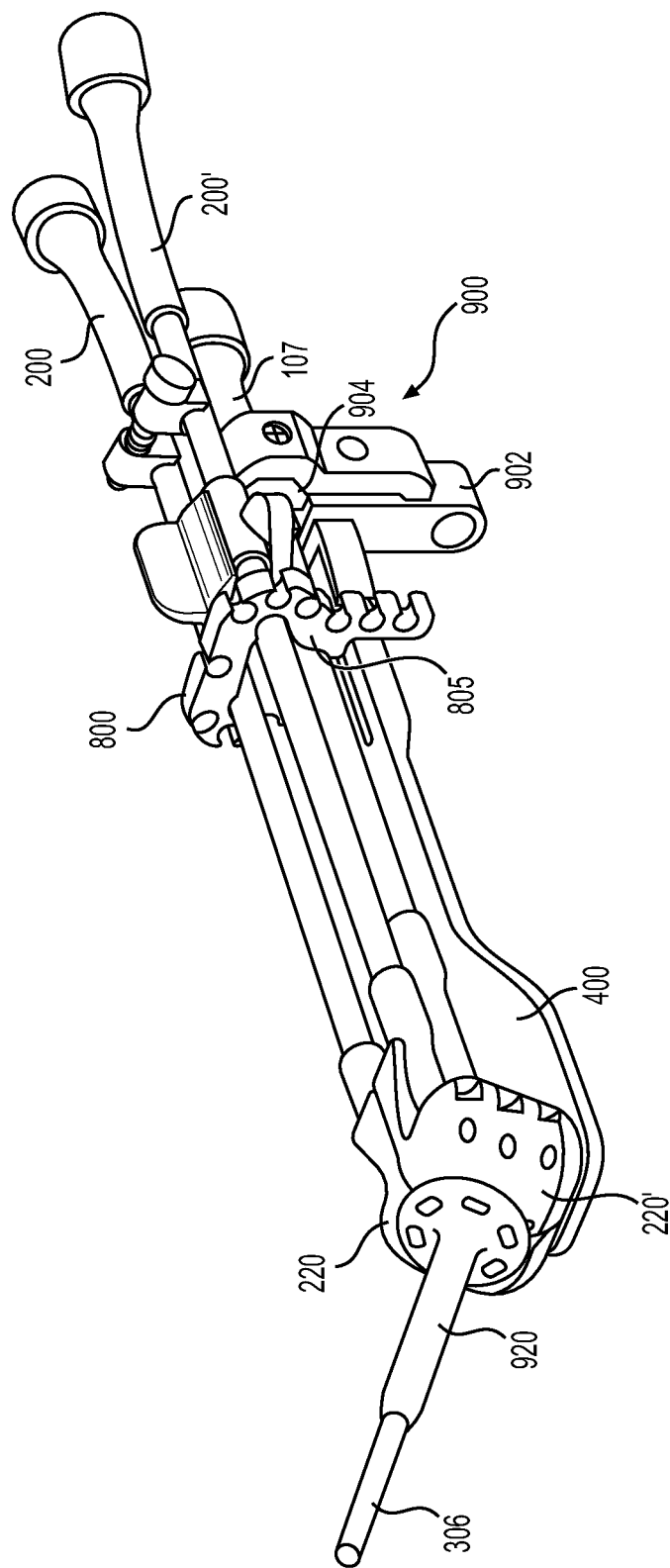
FIG. 20 illustrates a perspective view of the modular applicator shown in FIG. 18 with the sleeve shown in FIG. 20 coupled thereto.

As seen in FIGS. 19 and 20, in some embodiments, a sleeve 920 may be coupled to a modular applicator. Sleeve 920 may include a body 922 extending outwardly from a base 928 and a distal opening 924. Distal opening 924 may be sized to receive one or more peripheral elements therethrough (e.g., guide tube 600, needle 300, etc.).

Base 928 may define a planar surface that extends out from a proximal end of body 922 and may include one or more apertures 929 formed therethrough. The one or more apertures 929 of base 928 may be sized to receive one or more fasteners therethrough for securing sleeve 920 to a subject, such as, for example, by receiving one or more sutures therethrough to secure sleeve 920 to the subject. By way of example, base 928 of sleeve 920 may be stitched to a uterine mouth with body 922 received within a cervix of the subject. With sleeve 920 secured to a subject, insertion of the modular applicator into the subject may be facilitated by aligning needle 300 with distal opening 924 of elongated body 922.

It should further be understood that one or more components of modular applicators shown and described herein may be formed of non-metal components (i.e., magnetic resonance (MR) imaging safe materials). Further, although not necessarily shown in the figures, it should be appreciated that one or more components of modular applicators described herein may include one or more MM-compatible markers (or CT markers, X-ray markers, etc.) to facilitate an MR or other medical imaging of the components of the modular applicator. In this instance, the components of modular applicators, including MR markers or markers compatible with other medical imaging, may serve as anchor points for purposes of positioning modular applicators relative to a target treatment site within a subject under the assistance of medical imaging.

In some aspects, a proximal end of interstitial tube 100 or IU tube 107 may be key coded with one or more characters to promote proper connection of interstitial tube 100 with an after-loading device for receiving a radioactive source therefrom.

In some embodiments, ovoid tubes 200, 200' may include one or more identifying indicia positioned thereon (e.g., markings, labels, signs, etc.) that may provide a reference for coupling, e.g., ovoid tube 200 with an ovoid 220. In some embodiments, the one or more identifying indicia may include one or more MM markers, CT markers, X-ray markers, or markers that are compatible with one or more suitable medical imaging modalities.

Likewise, in some embodiments, ovoids 220, 220' may include one or more identifying indicia positioned thereon (e.g., markings, labels, signs, etc.) that correspond to indicia included on ovoid tube 200 for purposes of matching corresponding ovoids 220 and ovoid tubes 200 to one another (e.g., a right-hand ovoid tube 200 to a right-hand ovoid 220, a left-hand ovoid tube 200 to a left-hand ovoid 220, etc.). In some embodiments, the one or more identifying indicia may include one or more MIll markers, CT markers, X-ray markers, or markers that are compatible with one or more suitable medical imaging modalities.

The embodiments described above and illustrated in FIGS. 1-20 are merely exemplary. Any one or more previously described components, including, but not limited to, interstitial tube 100, IU tube 107, ovoid tube 200, 200', ovoids 220, 220', second connector 250, 250', needle 300, rectal retractor 400, first connector 500, 500', 550, 550', guide tube 600, spreading clip 700, 720, 740, bracelet device 800, clamp assembly 900, sleeve 920, and/or any other suitable brachytherapy component may be coupled together interchangeably to create modular applicators in accordance with the spirit of this disclosure. Thus, while certain embodiments have been described, those skilled in the art will recognize that other and further modifications may be made thereto without departing from the spirit of the disclosure, and it is intended to claim all such changes and modifications as falling within the scope of the disclosure.

The above disclosed subject matter is to be considered illustrative, and not restrictive, and the appended claims are intended to cover all such modifications, enhancements, and other implementations that fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description. While various implementations of the disclosure have been described, it will be apparent to those of ordinary skill in the art that many more implementations and implementations are possible within the scope of the disclosure. Accordingly, the disclosure is not to be restricted except in light of the attached claims and their equivalents.

What is claimed is:

1. A brachytherapy applicator comprising:
an interstitial tube, wherein the interstitial tube includes:
   a body having a proximal end and a distal end;
   a central conduit extending from the distal end of the body, wherein the central conduit includes a proximal opening, a distal opening located at a distalmost end of the brachytherapy applicator, and a channel extending from the proximal opening to the distal opening, and wherein the proximal opening is offset vertically from an axis of the body; and
at least one ovoid tube coupled to the interstitial tube and offset peripherally from the axis of the body, wherein the at least one ovoid tube is configured to support an ovoid at a distal end thereof;
wherein the proximal opening is configured to fluidly connect to a brachytherapy guide tube, and wherein the central conduit is configured to receive at least one of a needle or a catheter through the brachytherapy guide tube and the channel, bypassing the body.

2. The brachytherapy applicator of claim 1, further comprising a first connector attached to the body of the interstitial tube, the first connector having a first coupling surface that is configured to receive a second connector associated with the at least one ovoid tube to couple the at least one ovoid tube to the interstitial tube.

3. The brachytherapy applicator of claim 2, wherein the first connector includes a plurality of coupling surfaces, each having an aperture.

4. The brachytherapy applicator of claim 3, wherein the at least one ovoid tube includes a first ovoid tube and a second ovoid tube, wherein a second connector of the first ovoid tube is configured to releasably couple with the first coupling surface, and wherein a second connector of the second ovoid tube is configured to releasably couple with a second coupling surface of the plurality of coupling surfaces.

5. The brachytherapy applicator of claim 4, wherein the first ovoid tube includes a first ovoid located at a distal end of the first ovoid tube, and wherein the second ovoid tube includes a second ovoid located at a distal end of the second ovoid tube, and wherein the first ovoid and the second ovoid cooperatively form a generally rectangular surface aligned around a collar of the central conduit when the second connector of the first ovoid tube and the second connector of the second ovoid tube are coupled with the first connector of the interstitial tube.

6. The brachytherapy applicator of claim 2, further comprising a rectal retractor configured to removably couple to the first connector, wherein at least one of a proximal end of the rectal retractor or a distal end of the rectal retractor has a width that is greater than a width of a central portion of the rectal retractor.

7. The brachytherapy applicator of claim 1, further comprising at least one of a needle or a catheter having a distal portion dimensioned to extend into the proximal opening of the central conduit and through the central conduit so that a distal end of the needle or the catheter extends distally out of the distal opening of the central conduit when the needle or the catheter is positioned within the central conduit.

8. The brachytherapy applicator of claim 1, further comprising a joint located at the distal end of the body, wherein the joint has a proximal surface having an opening for coupling to a brachytherapy guide tube.

9. A brachytherapy applicator comprising:
an interstitial tube including:
   a body having a proximal end and a distal end;
   a joint located at a distal region of the body, wherein the joint has a proximal surface having an opening for coupling to a brachytherapy guide tube, wherein the opening is offset from an axis of the body; and a central conduit extending distally from the joint, wherein the central conduit has a channel therethrough that fluidly connects with the opening in the joint and extends through a distal end of the central conduit so that the distal end of the central conduit is open, wherein the distal end of the central conduit is located at a distalmost end of the brachytherapy applicator;

a first ovoid tube having a first ovoid located at a distal end of the first ovoid tube; and a second ovoid tube having a second ovoid located at a distal end of the second ovoid tube;

wherein the first ovoid and the second ovoid cooperatively form a generally rectangular surface aligned around the central conduit when the first ovoid tube and the second ovoid tube are connected to the interstitial tube, and wherein the central conduit is configured to receive at least one of a needle or a catheter through the brachytherapy guide tube and the channel, bypassing the body.

10. The brachytherapy applicator of claim 9, further comprising:
a first connector attached to a central region of the body, wherein the first connector has at least two coupling surfaces, and each coupling surface has an aperture therethrough;
a second connector having an anchor extending therefrom associated with the first ovoid tube; and
a second connector having an anchor extending therefrom associated with the second ovoid tube;
wherein each aperture of the at least two coupling surfaces is dimensioned to receive one of the anchors of the second connectors within it to releasably couple the first ovoid tube or the second ovoid tube to the interstitial tube.

11. The brachytherapy applicator of claim 10, further comprising a rectal retractor configured to removably couple to the first connector, wherein at least one of a proximal end of the rectal retractor or a distal end of the rectal retractor has a width that is greater than a width of a central portion of the rectal retractor.

12. The brachytherapy applicator of claim 9, further comprising a spreading clip.

13. A kit for forming a modular brachytherapy applicator, the kit comprising:
an interstitial tube having:
a body having a proximal end and a distal end; and
a central conduit extending from the distal end of the body, wherein the central conduit includes a proximal opening, a distal opening located at a distalmost end of the brachytherapy applicator, and a channel extending from the proximal opening to the distal opening, and wherein a proximal end of the central conduit where the proximal opening is located is offset from an axis of the body;
a first ovoid tube;
a first ovoid;
a second ovoid tube; and
a second ovoid;
wherein the proximal opening is configured to fluidly connect to a brachytherapy guide tube, and wherein the central conduit is configured to receive at least one of a needle or a catheter through the brachytherapy guide tube and the channel, bypassing the body.

14. The kit of claim 13, further comprising a needle or a catheter having an outer diameter that is less than an inner diameter of the central conduit.

15. The kit of claim 13, further comprising a first connector coupled to the body of the interstitial tube, the first connector having a first coupling surface and a second coupling surface, wherein a second connector associated with the first ovoid tube is configured to releasably couple with the first coupling surface, and a second connector associated with the second ovoid tube is configured to releasably couple with the second coupling surface.

16. The kit of claim 15, wherein the first ovoid and the second ovoid cooperatively form a generally rectangular surface aligned around a collar located at a distal end of the central conduit when the second connector of the first ovoid tube is coupled to the first coupling surface and the second connector of the second ovoid tube is coupled to the second coupling surface.

17. The kit of claim 13, further comprising a rectal retractor configured to removably couple to a first connector, wherein at least one of a proximal end of the rectal retractor or a distal end of the rectal retractor has a width that is greater than a width of a central portion of the rectal retractor.

18. The kit of claim 13, wherein the first ovoid and the second ovoid are configured to releasably couple to the first ovoid tube or the second ovoid tube, respectively.

19. The kit of claim 13, further comprising a joint located at a distal region of the body, wherein the joint has a proximal surface that includes an opening configured to couple with a distal end of a brachytherapy guide tube, wherein the central conduit extends from a distal surface of the joint, and wherein the opening of the joint communicates with the channel of the central conduit.

20. The kit of claim 19, further comprising the guide tube having the distal end configured to couple with the opening of the joint.

21. The kit of claim 13, wherein the first ovoid is coupled to a distal end of the first ovoid tube, and the second ovoid is coupled to a distal end of the second ovoid tube.

* * * * *